(12) United States Patent
Casteilla et al.

(10) Patent No.: US 8,945,920 B2
(45) Date of Patent: Feb. 3, 2015

(54) METHOD FOR CULTURING CELLS DERIVED FROM THE ADIPOSE TISSUE AND USES THEREOF

(75) Inventors: Louis Casteilla, Escalquens (FR); Valérie Planat-Benard, Lacroix Falgarde (FR); Luc Penicaud, Toulouse (FR); Carine Chanut, Ramonville St Agne (FR)

(73) Assignee: Centre National de la Recherche Scientifique, Paris (FR)

(*) Notice: Subject to any disclaimer, the term of this patent is extended or adjusted under 35 U.S.C. 154(b) by 344 days.

(21) Appl. No.: 12/161,975

(22) PCT Filed: Jan. 26, 2007

(86) PCT No.: PCT/FR2007/000158
§ 371 (c)(1),
(2), (4) Date: Dec. 10, 2008

(87) PCT Pub. No.: WO2007/085745
PCT Pub. Date: Aug. 2, 2007

(65) Prior Publication Data
US 2009/0246182 A1   Oct. 1, 2009

(30) Foreign Application Priority Data
Jan. 26, 2006   (FR) ...................................... 06 00710

(51) Int. Cl.
*C12N 5/00* (2006.01)
*C12N 5/077* (2010.01)
*A61K 35/12* (2006.01)

(52) U.S. Cl.
CPC .............. *C12N 5/0657* (2013.01); *A61K 35/12* (2013.01); *C12N 2506/1384* (2013.01)
USPC ............ 435/373; 435/377; 435/378; 435/383

(58) Field of Classification Search
None
See application file for complete search history.

(56) References Cited

U.S. PATENT DOCUMENTS

2003/0082152 A1   5/2003   Hedrick et al.
2008/0206208 A1*  8/2008   Casteilla et al. ............. 424/93.7

FOREIGN PATENT DOCUMENTS

| WO | WO 95/20042 | 7/1995 |
| WO | WO 02/055678 | 7/2002 |
| WO | WO 2005/042730 | 5/2005 |

OTHER PUBLICATIONS

Perez-Terzic et al. Cir Res 2003;92:444-52.*
Wang et al. Stem Cells 2006;24:1779-88.*
Casteilla et al. English Translation of WO 02/055,678A1, 2002.*
International Search Report for PCT/FR2007/000158 filed Jan. 26, 2007.
Planat-Benard V et al: "Spontaneous Cardiomyocyte Differentiation From Adipose Tissue Stroma Cells"; Circulation Research; vol. 94, No. 2; Feb. 6, 2004; pp. 223-229; XP002400832.
Fortier Lisa A: "Stem Cells: Classifications, Controversies, and Clinical Applications"; Veterinary Surgery vs. The Official Journal of the American College of Veterinary Surgeons Sep.-Oct. 2005, vol. 34, No. 5, Sep. 2005; pp. 415-423; SP002411799.
Cousin, B., et al., "Reconstitution of lethally irradiated mice by cells isolated from adipose tissue," *Biochem Biophys Res Commun*, 2003, vol. 301, pp. 1016-1022.
Erickson, G.R., et al., "Chondrogenic Potential of Adipose Tissue-Derived Stromal Cells in Vitro and in Vivo," *Biochem Biophys Res Commun*, 2002, vol. 290, pp. 763-769.
Lev, S., et al., Differentiation Pathways in Human Embryonic Stem Cell-Derived Cardiomyocytes, *Ann NY Acad Sci*, vol. 1047, pp. 50-65.
Safford, K.M., et al., "Neurogenic differentiation of murine and human adipose-derived stromal cells," *Biochem Biophys Res Commun* 2002, vol. 294, pp. 371-379.
Zuk, P.A., et al., "Human Adipose Tissue Is a Source of Multipotent Stem Cells," *Mol Biol Cell*, 2002, vol. 13, pp. 4279-4295.

* cited by examiner

*Primary Examiner* — Janice Li
(74) *Attorney, Agent, or Firm* — Alston & Bird LLP

(57) ABSTRACT

The invention concerns a method for culturing cells derived from the adipose tissue and in particular the stromal vascular fraction (SVF) to induce formation of cardiomyocytes, the use of the cells obtained by said culture method to reconstitute an ischemized cardiac zone, in particular following an infarction, as well as a pharmaceutical composition containing said cells. The method for obtaining cardiac cells comprises at least the following steps: a) selecting cardiomyogenic cells from the stromal vascular fraction (SVF); b) culturing the cells selected at step a) in a liquid medium optimized for expanding ex vivo the cardiomyogenic cells; c) maintaining and expanding said cells by successive passes in the liquid medium; and d) obtaining cardiac cells.

29 Claims, 12 Drawing Sheets

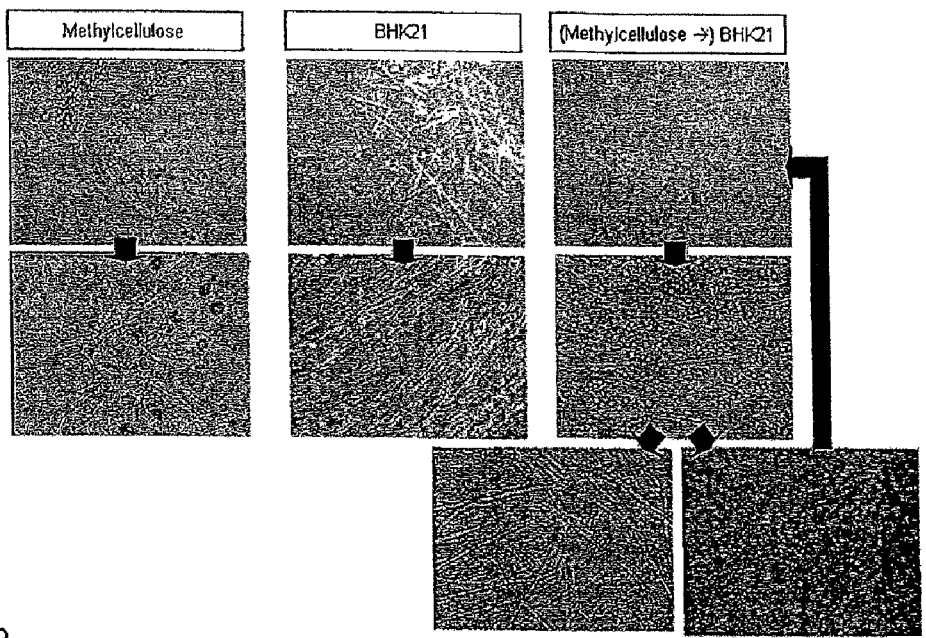
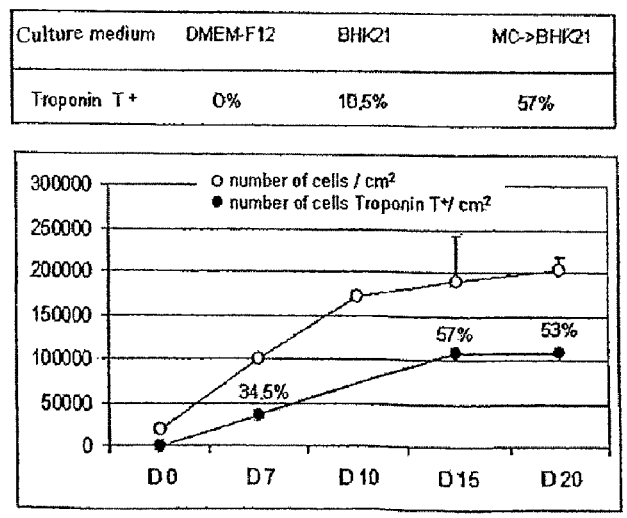
FIGURE 1

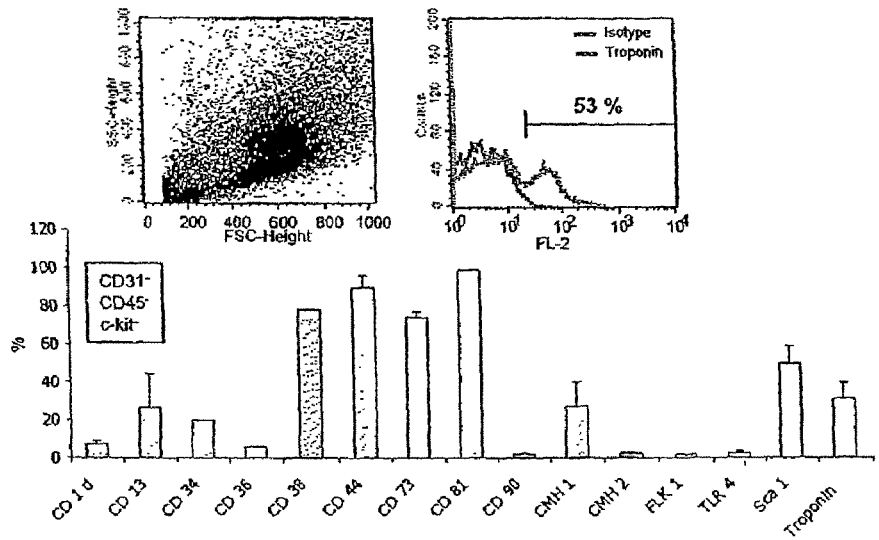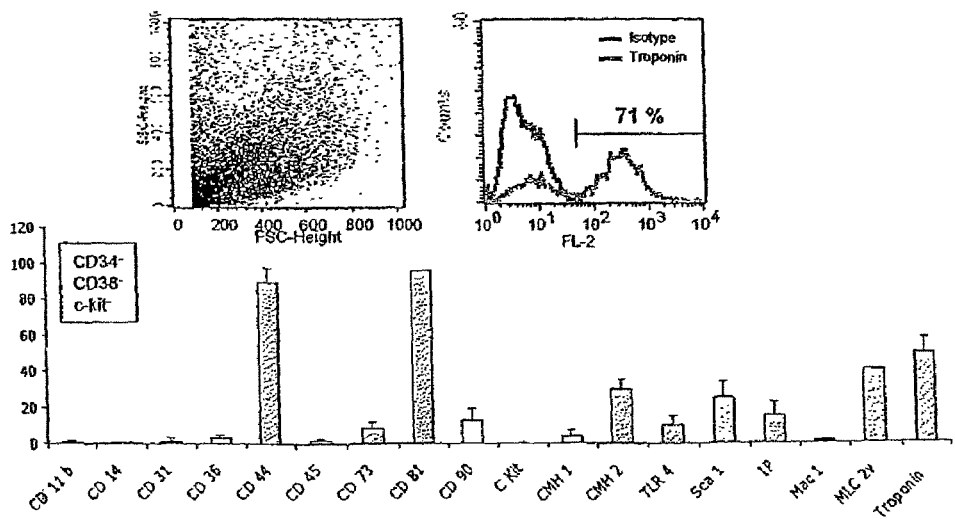
FIGURE 2.1

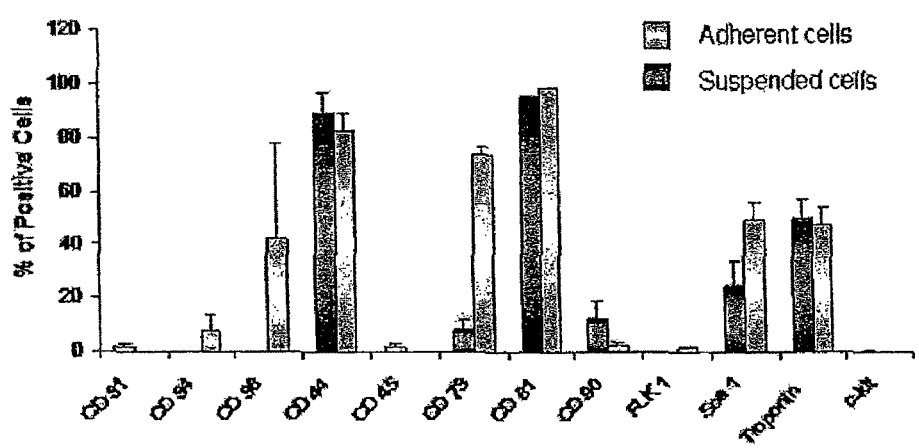
FIGURE 2.2

METHOD FOR CULTURING CELLS DERIVED FROM THE ADIPOSE TISSUE AND USES THEREOF

CROSS REFERENCE TO RELATED APPLICATIONS

This application is a national stage application filed under 35 U.S.C. 371 of International Application No. PCT/FR2007/000158, filed Jan. 26, 2007, which claims priority from French patent application 06 00710, filed Jan. 26, 2006.

FIELD AND BACKGROUND OF THE INVENTION

The present invention relates to a method for culturing cells derived from adipose tissue, and in particular from the stromal vascular fraction (SVF), to induce the formation of cardiomyocytes.

The subject of the present invention is also the use of the cells obtained by means of the culture method as defined above for reconstituting a cardiac region that has been rendered ischemic, in particular after an infarction, and also a pharmaceutical composition containing said cells.

In many cases, heart failure develops following an ischemic event (myocardial infarction) and is associated with a considerable loss of cardiomyocytes and with ischemia, which is not counterbalanced by the normal renewal of differentiated cardiomyocytes by the heart.

The means that exist for reconstituting cardiomyocytes are essentially based on strategies including a cell therapy, in order to improve the defective contractile performance and cardiac function (Wollert et al., *Circulation*, 2005, 112, 2, 151-153).

They essentially comprise:
- the transplantation of autologous myoblasts or of satellite cells, which improve cardiac function, even though the cells maintain their characteristics of muscle cells in the ischemic heart. Nevertheless, the apparent absence of connections between the grafted myoblasts and the resident cardiomyocytes excludes a synchronized contribution by the grafted cells to the function of the systolic pump;
- the concept of cell plasticity has opened up new perspectives in the field of heart failure and has resulted in various cells being used in the hope that these ectopic cells can transdifferentiate into cardiomyocytes, when they are placed in an appropriate in vivo context. In fact, initial studies have suggested that mesenchymal stem cells from the bone marrow and hematopoetic cells can transdifferentiate into cardiomyocytes; however, this phenomenon is currently disputed as is the concept of cell plasticity;
- another approach, which is less complicated, has been recommended and proposes to use cells involved in the cardiomyocyte transformation process, such as resident cardiomyocyte stem cells, fetal cells, embryonic cells or other cells such as bone marrow mesenchymal cells or endothelial cells (Kehat et al., J. Clin. Invest., 2001, 108, 407-444; Muller et al., FASEB J., 2000, 14, 2540-2558; Toma et al., Circulation, 2002, 105, 93-98; Liechty et al., Nat. Medecine, 2000, 11, 1282-1286; Conderelli et al., PNAS, 2001, 98, 10733-10738; Wang et al., J. Thorac. Cardiovasc. Surg 2001, 122, 699-705; Jackson et al., J. Clin. Invest. 2001, 107, 1395-1402). Two hypotheses have been put forward to explain these results: cells close to the totipotence of embryonic cells persist in adult tissues (brain, muscle, etc.) and are capable of differentiating into various cell types, or else specialized stem cells of these tissues possess great plasticity and are capable of dedifferentiating or being reprogrammed (transdifferentiation). These results have important consequences for the treatment of functional muscle defects (myopathies and cardiomyopathies) and diseases related to muscle degeneration (myocardium infarction). However, in practice, the effective reconstruction of cardiac muscle tissues from the abovementioned cells is difficult to carry out owing to the technical difficulties in sampling and the small amounts of tissues available. In addition to these technical difficulties, there are also ethical problems associated with the use of embryonic tissues (M/S, 2004, 6-7, 20, 651-661).

In this context, there exists a real need for new means and in particular for new sources of cells capable of effectively reconstructing the myocardium, which are effective and simpler to implement than the existing means.

Consequently, the inventors gave themselves the aim of providing cells capable of reconstituting cardiac muscle tissues in a long-lasting manner, the cells being isolated from tissues that are easy to sample and available in large amounts.

In the context of their previous research, the inventors have found (application WO 02/055678) that spontaneous differentiation of cells derived from adipose tissue, and more particularly of cells of the stromal vascular fraction (SVF), into functional cardiomyocytes exists when these cells derived from adipose tissue are cultured in a medium containing methylcellulose (PCT International application WO 02/055678; Planat et al., Circ. Res., 2004, 94, 223-229).

Thus, PCT International application WO 02/055678 recommends, in order to obtain differentiation of SVF cells into cardiogenic cells, a step of preparing the SVF, a cell-sorting step (selection) comprising culturing the cells on a semi-solid medium (methylcellulose) and/or purifying the cells by physical separation and immunoselection (antibodies) and a step for "expanding" the cells in DMEM-F12 liquid medium. However, it is found that culturing in a DMEM-F12 liquid medium in fact only makes it possible to maintain the cardiomyogenic cells and not to expand them (Planat-Bénard et al., Circ. Res., 2004, 94, 223-229).

In fact, the abovementioned article in the names of Planat-Bénard et al. shows that the cells of the SVF are capable of spontaneously differentiating into cardiomyocytes when they are cultured in a medium containing methylcellulose. It is also specified that these cells can be maintained for several months on methylcellulose or in a DMEM-F12 liquid culture medium.

Thus, this article shows that cells of cardiomyocyte type can be obtained spontaneously in primary culture from the SVF when a semi-solid medium based on methylcellulose is used as culture medium. On the other hand, when the DMEM-F12 liquid medium is used, very few contractile cells are observed.

Thus, although both the method described in PCT International application WO 02/055678 and that recommended in the abovementioned article in the names of Planat-Bénard et al. make it possible to effectively obtain cardiomyocytes, they do not give a good differentiation yield. This is because the frequency of obtaining cardiomyocytes both in the method described in PCT International application WO 02/055678 and in the article in the names of Planat-Bénard et al. is very low; this is in particular due to the heterogeneity of the SVF cells and to the variability in their preparation, which do not make it possible to obtain, under the standard culture conditions described above, a good yield in terms of differentiation of these cells into cardiac cells.

SUMMARY OF THE INVENTION

Since, under the abovementioned conditions, this differentiation is rare, the inventors have now developed a method of expansion in vitro which has a very good yield of cardiomyogenic cells, from adipose tissue, and more particularly from the stromal vascular fraction.

Thus, the pending application gave itself the aim of obtaining cardiac cells, from SVF, with a high yield for the purpose of the therapeutic use thereof.

The inventors have found, unexpectedly, that the cells thus obtained survive, can be grafted and differentiate into cardiomyocytes after they have been implanted into an animal model (mouse presenting an acute ischemia), in comparison with adipose tissue cells in culture, not transformed into cardiomyocytes.

For the purpose of the present invention:
the term "cardiomyogenic cells" is intended to mean any cell capable of differentiating into a cell of cardiac type, including cardiac progenitors (precursor cells present in the heart);
the term "cardiomyocytes" is intended to mean contractile cardiomyocytes of cylindrical shape having connections with the adjacent myocardial cells, so as to form a complex three-dimensional network;
the term "cells of cardiac type" (or cells with a cardiac phenotype) is intended to mean cells expressing cardiac proteins (troponin T); these are cells undergoing cardiac differentiation; they differ from cardiomyogenic cells per se, which have a cardiac potential, i.e. are capable of entering into a cardiac differentiation pathway;
the term "cell expansion": it is considered that there is cell expansion when some cells of a cell culture are removed and seeded into a new culture medium, and then proliferate. When this operation is carried out only once, this is a single pass. When this operation is carried out several times (seeding and cell division), successive passes are thus carried out;
the term "cell maintenance": cell culture without passes.

Hereinafter, the expression "cardiac cells" (alternatively cardiogenic cells) includes both cardiomyogenic cells, cardiac progenitors, cells of cardiac type and cardiomyocytes.

Adipose tissue exists in various forms in mammals: extramedullary white adipose tissue, which represents the principle storage organ of the organism, medullary white adipose tissue, the exact role of which is unknown, and thermogenic brown adipose tissue.

Due to its considerable expansion potential, which persists throughout the life of the individual, white adipose tissue in adults constitutes a source of abundant cells that are easy to obtain.

This white adipose tissue consists of two cell fractions:
an adipocyte fraction which represents 30% to 60% of the cells of the adipose tissue and is characterized by the accumulation of triglycerides (floating cell fraction). This fraction is composed predominantly (99%) of differentiated adipocytes and of some contaminating macrophages, rich in lipid droplets, and
a nonadipocyte fraction, called stromal vascular fraction (SVF), comprising some blood cells, some mature endothelial cells (cells of the microvascular endothelium: $CD31^+$, $CD144^+$), pericytes, fibroblasts and pluripotent stem cells.

It has been shown that the stromal vascular fraction, conventionally used to study the differentiation of preadipocytes to mature adipocytes, is a source of pluripotent cells comprising, in addition to the adipocyte progenitors (preadipocytes), endothelial, hematopoetic and neurogenic progenitors, and also mesenchymal stem cells capable of differentiating into osteogenic, chondrogenic and myogenic lines (Planat-Bénard V. et al., *Circulation*, 2004, 109, 656-663; Zuk PA. et al., *Mol. Biol. Cell*, 2002, 13, 4279-95; Erickson GR. et al., *Biochem. Biophys. Res. Commun.*, 2002, 290, 763-9; Cousin B. et al., *Biochem. Biophys. Res. Commun.*, 2003, 301, 1016-22; Safford K. et al., *Biochem. Biophys. Res. Commun.*, 2002, 294, 371-9; PCT International application WO 02/055678 and American application US 2003/0082152).

These two cell fractions can be separated by virtue of their difference in density, according to methods such as those described by Björntorp et al. (J. Lipid. Res., 1978, 19, 316-24).

The inventors have now developed culture conditions which significantly increase the number of SVF cells capable of transforming (or of transdifferentiating) into cells with a cardiac phenotype:
either directly from the freshly prepared crude SVF, by means of at least one phenotypic marker, which makes it possible to directly select a population of interest (MHC1-negative sorting, for example), followed by culturing in a suitable liquid medium,
or after primary culturing of the freshly prepared crude SVF in a semi-solid medium, followed by secondary culturing of the cells obtained in a suitable liquid medium; in this case, cell sorting may also be carried out before the secondary culturing.

The presence of cardiac cells in adipose tissue is surprising and the signals involved in the transformation of the resident quiescent cells into cells having a contractile cardiac phenotype was not known up until now.

TGFβ and $H_2O_2$ were described as being effective in promoting the differentiation of neonatal cardiomyocytes and of embryonic stem cells, but did not allow the induction of such a transformation from cells derived from adipose tissue.

Among the factors tested (IL3, IL6, SCF, BMP2, TGFβ, 5-azacytidine), only the presence of β-mercaptoethanol is necessary, but not sufficient.

A subject of the present invention is therefore a method for obtaining cardiac cells, characterized in that it comprises at least the following steps:
a) selecting cardiomyogenic cells from the crude stromal vascular fraction (SVF);
b) culturing the cells selected in step a) in a liquid medium optimized for expanding the cardiomyogenic cells ex vivo, said liquid medium being selected from the group consisting of BHK21 medium containing at least fetal calf serum and β-mercaptoethanol and any other medium, the composition of which is of the same type as that of BHK21 medium as regards the composition of inorganic salts, amino acids and vitamins;
c) maintaining and expanding said cells by successive passes in the liquid medium; and
d) obtaining cardiac cells.

Thus, the cells of the SVF represent a heterogeneous cell population which can be used directly (freshly prepared crude SVF fraction) or after culturing.

The cells of the SVF after primary culturing correspond to a subpopulation of adherent cells (fraction of adherent cells of the SVF, also known as ADSC for adipose-derived stromal cells).

Advantageously, said culturing of cells selected in step a) is carried out in a liquid medium as defined above and on an appropriate adhesion surface (of the type gelatin, adhesion proteins, extracellular matrix proteins). For example, said culturing is carried out in dishes coated with gelatin and containing a BHK21 medium. In fact, the adhesion properties of the cardiogenic cells of interest and the liquid culture medium used for the expansion are important.

The primary culturing in methylcellulose until the appearance of contractile elongated cells makes it possible to select cells which are capable of initiating a cardiac differentiation program.

These cells are seeded into a BHK21 liquid medium. A cell expansion is obtained by seeding the cells in suspension (no proteolytic treatment) into a BHK21 medium every two days.

In vitro, both cardiomyogenic cells per se (precursors capable of entering into a cardiac differentiation pathway) and cardiac-type cells (cells undergoing cardiac differentiation) are obtained; in fact, the cardiomyogenic cells that are obtained in vitro mostly differentiate into cardiac-type cells, but the differentiation in vitro is never as successfully completed as that obtained in vivo; in vivo, cardiomyocytes are obtained.

Said cardiac cells can advantageously be conserved in frozen form.

In a first advantageous embodiment of said method (method 1), the selection in step a) is carried out by primary culture of cells of the crude stromal vascular fraction (SVF) in a semi-solid medium, until the emergence of clusters (or clones) of contractile cells; in this case:
  step b) comprises sampling said contractile cells consisting of two subpopulations having distinct morphological types, namely adherent cells of elongated type and nonadherent cells of round (or rounded) type; and subculturing said contractile cells in a liquid medium optimized for expanding the cardiomyogenic cells or the embryonic stem cells (cells of ES type), ex vivo; preferably, step b) of culturing the cells selected in a) is carried out in a BHK21 liquid medium containing at least fetal calf serum and β-mercaptoethanol and any other medium, the composition of which is of the same type as that the BHK21 medium as regards the composition of inorganic salts, amino acids and vitamins, and on an adhesion surface suitable for expanding the cardiomyogenic cells ex vivo;
  step c) comprises maintaining and expanding at least one of the two subpopulations of cells (adherent cells and nonadherent cells in suspension) by successive passes in liquid medium;
  the semi-solid medium is advantageously selected from the group consisting of cellulosic derivatives (in particular, methylcellulose) and reconstituted basal membrane matrices comprising at least one of the following elements: collagen, laminin and proteoglycans (Matrigel, for example).

The adherent cells and the nonadherent cells (or cells in suspension in the liquid medium) have at least the following characteristics: these two cell types are: $CD44^+$, $CD81^+$, CD31, CD45, ckit; at least 50% of the two populations are positive for Sca-1 and troponin T. These two populations are also $CD90^-$, $Flk1^-$ and $MLC2v^-$.

Thus, these two populations express $CD44^+$ and $CD81^+$, but do not express $CD31^-$, $CD34^-$, $CD45^-$, $CD90^-$, $CD117^-$ (c-kit) or $Flk1^-$.

This antigen phenotype is very particular.

These two populations are also positive for CD29 (adherent cells: 98%; nonadherent cells: 89%); this marker is not, however, specific for these cells.

The major difference between the two cell types is the following: the adherence cells are positive for CD38 and CD73 and some (20%) express CD34, and are negative for MHC2, whereas the nonadherent cells are $MHC1^-$.

Advantageously, the crude stromal vascular fraction cultured in semi-solid medium containing in particular methylcellulose, followed by subculturing of the contractile clusters in liquid medium such as BHK21 medium, containing at least fetal calf serum and β-mercaptoethanol, makes it possible to significantly optimize the transdifferentiation of the adipose tissue cells into cardiomyogenic cells in the culture in liquid medium. In fact, the primary culture step in semi-solid medium allows an effective selection of the cardiomyogenic cells from the stromal vascular fraction and provides, after seeding in liquid medium (secondary culture), a cell layer consisting of the two cardiomyogenic cell morphologies described (adherent and in suspension). This culture can be maintained in the long term (several months) by successive passes (mechanical or enzymatic), compared with direct seeding into BHK21 liquid medium.

Under these conditions, very good yields of cardiomyogenic cells are, surprisingly, obtained:
  from the cells in suspension: the adherent cell layer is obtained in a culture dish of varying diameter (30 mm in diameter, for example) and produces on average 150 000 cardiomyogenic cells every two days; the latter are found in suspension in the culture medium, throughout the period of viability of the cell layer, which subsequently ages (~20 days) and decreases its production;
  from the adherent cells: the floating cells recovered and placed in a new culture dish adhere and re-form an adherent layer in 12 days. Starting from 150 000 floating cells, a layer consisting of on average 900 000 adherent cells is obtained after 12 days.

According to an advantageous arrangement of this embodiment (method 1), the primary culture period according to step a) is a few days to a few weeks, preferably one to two weeks.

According to another advantageous arrangement of this embodiment (method 1), prior to subculturing the contractile cells, a second selection is carried out using at least one suitable marker; said marker is advantageously a positive marker (cardiac cell marker) and/or a negative marker for cardiac cells.

Among the positive markers for cardiac cells, mention may be made of: Sca-1, troponin, MLC2v, CD44, CD81, CD73 or CD38.

Among the negative markers for cardiac cells, mention may be made of the major histocompatibility complex MHC markers (MHC1 or MHC2), CD31, CD34, CD45, c-kit and Flk1.

Sorting using a negative and/or positive marker, carried out after culturing on a semi-solid medium, allows a spectacular enrichment in cardiomyogenic cells. For example, when 30 000 MHC1-negative cells, derived from the crude SVF, are seeded per ml of methylcellulose, this gives on average 30 clusters of cardiac type; consequently, 1 cell/1500 is responsible for a contractile cluster after 14 days of culturing.

According to another advantageous arrangement of this embodiment (method 1), the liquid medium of step b) is advantageously a BHK21 medium containing at least fetal calf serum and β-mercaptoethanol, or any other similar medium that can be used for ES-type cells; the composition of said medium is in particular the same type as that of BHK21 medium as regards the composition of inorganic salts, amino acids and vitamins.

In a second advantageous embodiment of said method (method 2), the selection in step a) is carried out by cell sorting of the cells from the crude SVF using at least one negative marker for cardiac cells, as defined above and therefore in particular selected from the group consisting of the major histocompatibility complex markers (MHC1 or MHC2) and CD31, CD34, CD45, c-kit and Flk1. In particular, the SVF cells capable of differentiating into cardiomyogenic cells are, surprisingly, MHC$^-$.

In this case, step b) comprises culturing the selected cells in a BHK21 liquid medium containing at least fetal calf serum and β-mercaptoethanol, or any other similar medium that can be used for ES-type cells, as specified above.

The sorting carried out with the negative marker for cardiac cells, and in particular the MHC sorting, is carried out using a fresh preparation of SVF. The yield of MHC1-negative cells obtained after cell sorting is variable, depending on the SVF preparations, and comprises, for example, 20% to 40% of MHC1$^-$ cells using freshly prepared crude SVF.

Whatever the method of implementing step a) (method 1 or method 2), step c) of maintaining and expanding the cardiomyogenic cells in cultures in liquid medium can be carried out according to one of the following two methods:
  centrifugation of the cells in suspension in a liquid medium identical to or different than that of step b) and re-seeding of the cell pellet in the same liquid medium; a new cell layer forms and again the two types of cell morphologies are found. The culture of the two types of morphologies can thus be maintained in the long term;
  enzymatic (of the trypsin type) detachment or any other method for detaching the cells of the adherent cell layer, centrifugation of the detached cell suspension and re-seeding of the cell pellet in the same liquid medium; similarly, a new cell layer forms and again the two types of cell morphologies are found.

The culture of the two types of morphologies can thus be maintained in the long term.

Preferably, the method according to the invention comprises:
a) a primary culture of SVF cells in a semi-solid medium based on methylcellulose and selection of the cardiomyogenic cells,
b) a secondary culture of the cells selected in a) in a
  BHK21 liquid medium containing at least fetal calf serum and β-mercaptoethanol, or any other medium, the composition of which is of the same type as that of the BHK21 medium as regards the composition of inorganic salts, amino acids and vitamins, and on an adhesion surface suitable for expanding the cardiomyogenic cells ex vivo,
c) maintaining and expanding said cells by successive passes in liquid medium, and
d) obtaining cardiac cells.

As a variant, steps a) and b) are combined and can be carried out by primary culture of the SVF cells in BHK21 medium and on an appropriate adhesion support or surface, such as gelatin, adhesion proteins and extracellular matrix proteins.

In accordance with the invention, the crude stromal vascular fraction is obtained, prior to step a), from deposits of adipose tissue by:
  isolation of the SVF by digestion with proteolytic enzymes and by physical separation, in particular by a combination of steps of centrifugation, and filtration and/or difference in density, and
  purification of the cells by physical separation (filtration and/or centrifugation) and/or immunoselection.

Said cardiomyogenic cells may also be genetically modified. Thus:
  they may comprise at least one mutation of an autologous gene or
  they may contain at least one copy of a heterologous gene.

Said genetically modified cells are preferably of human origin.

A subject of the present invention is also the use of the cardiac cells that can be obtained from the cells of the stromal vascular fraction, under the conditions set out in the methods as defined above (method 1 or method 2), for the preparation of a medicament capable of reconstituting an ischemic cardiac region.

According to an advantageous embodiment of said use, said cardiac cells are selected from the group consisting of:
(i) the adherent contractile cardiomyogenic cells of elongated shape having the following characteristics: CD38$^+$, CD44$^+$, CD73$^+$, CD81$^+$, CD31$^-$, CD45$^-$, Ckit$^-$, CD90$^-$, Flk1$^-$, MHC2$^-$, approximately 50% of said cells being Sca-1$^+$, troponin T$^+$ and MLC2v$^+$,
(ii) the nonadherent cells of rounded shape: CD44$^+$, CD81$^+$, CD31$^-$, CD45$^-$, CD73$^-$, CD90$^-$, Flk1$^-$, approximately 50% of said cells being Sca-1$^+$, troponin T$^+$, MLC2v$^+$ and MHC1$^-$,
the two types of cells also expressing the Brachyury mesodermal transcription factor, the Islet-1 and MEF-2c transcription factors and the Oct3/4 transcriptional binding factor, or
iii) a mixture of said adherent cells and of said nonadherent cells.

These two types of cells (adherent and nonadherent) are also CD34$^-$.

A subject of the present invention is also a pharmaceutical composition, characterized in that it comprises a mixture:
(i) of adherent cardiomyogenic cells of elongated shape having at least the following characteristics: CD38$^+$, CD44$^+$, CD73$^+$, CD81$^+$, CD31$^-$, CD45$^-$, Ckit$^-$, MHC2$^-$, approximately 50% of said cells being Sca-1$^+$, troponin T$^+$ and MLC2v$^+$, and
(ii) of nonadherent cells of rounded shape having at least the following characteristics: CD44$^+$, CD81$^+$, CD31$^-$, CD45$^-$, CD73$^-$, MHC1$^-$, approximately 50% of said cells being Sca-1$^+$, troponin T$^+$ and MLC2v$^+$,
the two types of cells also expressing the Brachyury mesodermal transcription factor, the Islet-1 and MEF-2c transcription factors and the Oct3/4 transcriptional binding factor, and at least one pharmaceutically suitable carrier.

According to an advantageous embodiment of said composition, it also comprises one or more cardiac factors.

According to an advantageous arrangement of this embodiment, said composition also comprises troponin T and/or MLC2v (Myosin Light Chain kinase 2v).

Said composition is administered via any route of administration. In particular, it is advantageously injected in situ (direct injection) using appropriate syringes or by means of an endoventricular or endocoronary catheter; it may also be injected intravenously or administered systemically.

As regards ischemic pathologies, the tissue mass to be reconstituted or to be implanted proves to be considerable on the cellular scale (20 to 30 cm$^3$). However, since this involves cells with a proliferative potential (demonstrated in vitro), the amounts to be injected are less than if it was a question of differentiated cells.

Thus, the method according to the invention makes it possible to obtain large amounts of cells with a cardiac potential.

Now, myocardial infarction is associated with a considerable loss of differentiated cardiomyocytes due to the ischemia. This loss cannot be compensated for by the natural renewal of the differentiated cardiomyocytes in the heart. The cells obtained according to the method according to the invention implanted into an acute ischemic environment survive and effectively acquire the characteristics of cardiac cells with beneficial effects, avoiding remodeling and deterioration of left ventricular function.

BRIEF DESCRIPTION OF THE DRAWINGS

In addition to the above arrangements, the invention also comprises other arrangements, which would emerge from the description which follows, which refers to exemplary embodiments of the method which is the subject of the present invention and also to the attached drawings, in which:

FIG. 1: FIG. 1A: Change in morphology of the cells of the SVF cultured under various conditions:
- in methylcellulose at an early stage (D7, top) and a more advanced stage (D30, bottom),
- in BHK21 liquid medium at an early stage (D7, top) and at more advanced stage (D15, bottom),
- in methylcellulose then BHK21 after selection, at an early stage (D7, top) and at more advanced stage (D15, middle), giving rise an adherent population (bottom, left) and a population in suspension (bottom, right) capable of self-maintaining the culture.

FIG. 1B: Percentage of cells expressing the troponin T cardiac marker under the various culture conditions (top) and change in the number of troponin $T^+$ cells under the culture conditions methylcellulose (MC)→BHK21.

FIG. 2: Phenotyping (FACS) of the two cell populations obtained under the culture conditions MC-BHK21. (A-B) Size/granulosity representation and troponin T labeling. (C) Expression of various cell markers.

EXAMPLES

Figure 3:
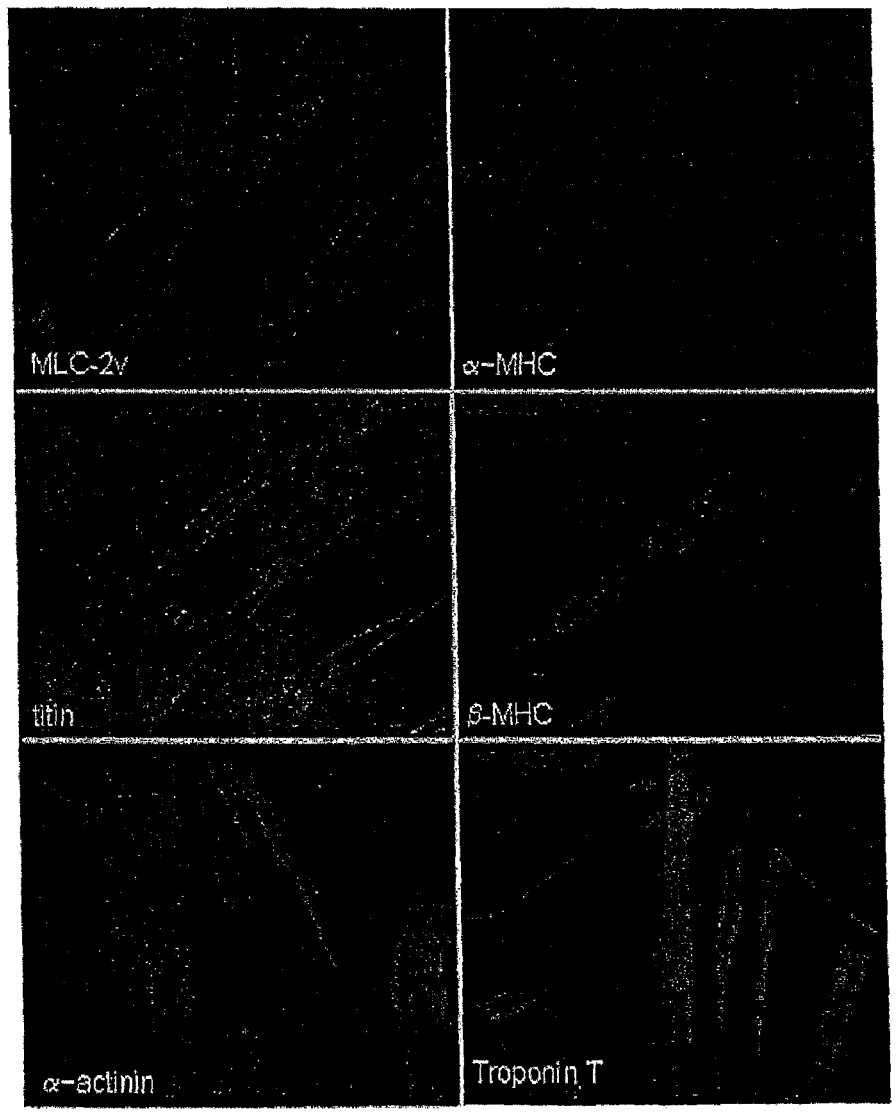
FIG. 3: In vitro cardiac differentiation of the adherent cells: immunocytochemisty showing that the cells express MLC-2v, titin, α-actinin, β-MHC and troponin T. The cells do not express α-MHC at this stage.

It should be understood, however, that these examples are given only by way of illustration of the subject of the invention, of which they in no way constitute a limitation.

Example 1

Materials and Methods

1) Animals and Tissue Samples

Male 8-week-old C57Bl/6 mice (Harlan, France) and male GFP mice are raised in a controlled environment (light/dark cycle of 12 h at 21° C.) with free access to water and to the standard food intake.

All the procedures are carried out in agreement with guideline EEC/No 07430.

At the end of the experiments, the mice are killed by cervical dislocation under anesthesia with $CO_2$.

The adipose tissue is rapidly removed and treated for the subsequent analyses.

2) Isolation of Adipose Tissue Cells

Method 1:

The cells are isolated from the adipose tissue of 5- to 8-week-old mice overall according to the method described by Björntorp et al., 1978, with minor modifications. The adipose tissue removed is dissected under a microscope in sterile dishes containing PBS, so as to remove all traces of muscle tissue, and then digested at 37° C. for 30 min, in digestion medium containing DMEM F12-0K, 2% BSA (bovine serum albumin) and 2 mg/ml of collagenase (reference SIGMA) at 10 ml of digestion medium per 3 g of tissue. The DMEM F12-OK medium comprises, per 500 ml of DMEM F12 (Gibco reference 31330 038), 5 ml of ASP (ready-to-use solution of antibiotics+antifungal: 0.25 µg/ml amphotericin, 100 µg/ml streptomycin, 100 µg/ml penicillin G) (SIGMA reference A7292), 0.016 mM of biotin (SIGMA reference B4639), 0.018 mM of pantothenic acid (SIGMA reference P5155) and 100 µM of ascorbic acid (SIGMA reference A4034). After removal of the undigested fragments by filtration (25 µm filters), the mature adipocytes are separated from the pellet containing the cells of the SVF by centrifugation (600 g, 10 min). The stromal vascular cells thus isolated are resuspended in DMEM-F12 culture medium and counted (manual counting on a grid cell counter or a Coulter particle counter).

Method 2:

The cells are isolated from the adipose tissue of 3-week-old mice and the process is carried out as described in method 1, using 10 ml of digestion medium per 1 g of adipose tissue. The digestion conditions are identical to those of method 1, the digestion medium is different. It contains 6.7 mM Hepes, 3 mM NaCl, 0.025 mM KCl, 0.078 mM $CaCl_2$, 4.5 mg/ml glucose, 1.5% BSA supplemented with 1 mg/ml of collagenase. As a variant, the digestion medium is a PBS buffer containing 2% of BSA and 2 mg/ml of collagenase (used in particular for interscapular brown adipose tissue extracted from GFP transgenic mice). After removal of the undigested fragments by filtration (25 μm filters), the mature adipocytes are separated from the pellet containing the cells of the SVF by centrifugation (1 000 g, 10 min).

The stromal vascular cells thus isolated are resuspended in DMEM-F12 culture medium and a further centrifugation is carried out (1 000 g, 10 min). The cells are resuspended in culture medium and counted as above.

3) Culturing on a Methylcellulose-Based Medium

The SVF cells isolated (freshly prepared crude SVF fraction) as specified in 2) are placed in culture (30 000 cells/ml) in a methylcellulose-based medium (Methocult GFM3534, StemCell Technologies, Vancouver) and maintained in culture for two weeks, during which time the morphology of the clones (or clusters) obtained is monitored.

The contractile clones are pinpointed, removed and washed in PBS.

After rapid centrifugation (5 min, 600 g), a cell suspension is prepared for subsequent use.

4) Procedure for Culturing Contractile Clones

A crude extract of SVF cells (32 000 cells/cm$^2$) or clones taken from the methylcellulose-based medium (1 500 cells/cm$^2$) are seeded into 30 mm dishes (Greiner Bio-One) coated with gelatin at 0.1%, and cultured in BHK21 medium (Gibco BRL), the precise composition of which is given in Tables I and II hereinafter, containing 10% of fetal calf serum (StemCell Technologies) and supplemented with $10^4$M of β-mercaptoethanol (Sigma), 2 mM of glutamine (Gibco BRL), 1 mM of pyruvate (Gibco BRL), 0.1 mM of nonessential amino acids (Gibco BRL) and a solution containing 0.25 μg/ml of amphotericin, 100 U/ml of penicillin G and 100 μg/ml of streptomycin (Sigma, APS solution).

Any other medium similar to the BHK21 medium, that can be used for ES-type cells, may also be used. The composition of said medium is in particular of the same type as that of the BHK21 medium as regards the composition of inorganic salts, amino acids and vitamins.

The cell expansion is carried out by harvesting the cells in suspension in the culture medium every three days. After centrifugation (600 g, 5 min), the cells are re-seeded into culture dishes 30 mm in diameter, coated with gelatin at 0.1%, and cultured in a BHK21 medium.

5) Culturing of Control Cells

The freshly prepared crude SVF cells are seeded into DMEM-F12 medium, the precise composition of which is given in Table III, supplemented with 10% of newborn calf serum, at a density of 30 000 cells/cm$^2$. These cells are known as ADSC cells (Adipose-Derived Stromal Cells).

For the controlled experiments, these cells are, in addition, treated as follows: after culturing for 6 hours, the nonadherent cells are removed by washing and the adherent cells are maintained in culture for six days until phenotyping or grafting (for expansion). The subconfluent cells are harvested by trypsinization for 5 min at 37° C., and constitute the SVF adherent cell fraction. These cells are transplanted into the mice.

TABLE I

Composition of the BHK21 liquid culture medium

| Ref. Components | 21710 (or any medium that can be used for ES-type cells) 1X liquid mg/L |
|---|---|
| INORGANIC SALTS: | |
| $CaCl_2 \cdot 2H_2O$ | 265.00 |
| $Fe(NO_3)_3 \cdot 9H_2O$ | 0.10 |
| KCl | 400.00 |
| $MgSO_4 \cdot 7H_2O$ | 200.00 |
| NaCl | 6400.00 |
| $NaHCO_3$ | 2750.00 |
| $NaH_2PO_4 \cdot 2H_2O$ | 141.00 |
| AMINO ACIDS: | |
| L-arginine•HCl | 42.00 |
| L-cystine | 24.00 |
| L-glutamine | 292.00 |
| L-histidine HCl•$H_2O$ | 21.00 |
| L-isoleucine | 52.00 |
| L-leucine | 52.00 |
| L-lysine•HCl | 73.00 |
| L-methionine | 15.00 |
| L-phenylalanine | 33.00 |
| L-threonine | 47.60 |
| L-tryptophan | 8.00 |
| L-tyrosine | 36.20 |
| L-valine | 46.80 |
| NONESSENTIAL AMINO ACIDS (see Table II) | 5 ml, 10 mM/500 ml |
| VITAMINS: | |
| Calcium pantothenate D | 2.00 |
| Choline chloride | 2.00 |
| Folic acid | 2.00 |
| i-inositol | 3.60 |
| Nicotinamide | 2.00 |
| Pyridoxal HCl | 2.00 |
| Riboflavin | 0.20 |
| Thiamine HCl | 2.00 |
| OTHER COMPONENTS: | |
| D-glucose | 4500.00 |
| Phenol red | 15.00 |
| L-glutamine | 5 ml, 200 mM/500 ml |
| β-mercaptoethanol | $10^{-4}$ M final |
| Pyruvate | 5 ml, 100 mM/500 ml |
| Antibiotics-antimycotics (amphotericin, streptomycin, penicillin) (ASP, Sigma A7292) | 1% |
| 10% ES serum (stem cells) | 10% l |

TABLE II

Nonessential amino acids

| Ref. Components AMINO ACIDS | 11140 100X liquid g/L |
|---|---|
| L-alanine | 890.00 |
| L-asparagine | 1320.00 |
| L-aspartic acid | 1330.00 |
| L-glutamic acid | 1470.00 |
| Glycine | 750.00 |
| L-proline | 1150.00 |
| L-serine | 1050.00 |

TABLE III

Composition of the DMEM-F12 liquid culture medium

| Compounds | Concentration (mg/l) |
|---|---|
| AMINO ACIDS: | |
| Glycine | 18.75 |
| L-alanine | 4.45 |
| L-arginine hydrochloride | 147.5 |
| L-asparagine-$H_2O$ | 7.5 |
| L-aspartic acid | 6.65 |
| L-cysteine hydrochloride $H_2O$ | 17.56 |
| L-cystine 2HCl | 31.29 |
| L-glutamic acid | 7.35 |
| L-histidine hydrochloride $H_2O$ | 31.48 |
| L-isoleucine | 54.47 |
| L-leucine | 59.05 |
| L-lysine hydrochloride | 91.25 |
| L-methionine | 17.24 |
| L-phenylalanine | 35.48 |
| L-proline | 17.25 |
| L-serine | 26.25 |
| L-threonine | 53.45 |
| L-tryptophan | 9.02 |
| Dehydrated disodium salt of L-tyrosine | 55.79 |
| L-valine | 52.85 |
| VITAMINS: | |
| Ascorbic acid phosphate | 2.5 |
| Biotin | 0.0035 |
| Choline chloride | 8.98 |
| Calcium pantothenate D | 2.24 |
| Folic acid | 2.65 |
| i-inositol | 12.6 |
| Niacinamide | 2.02 |
| Pyridoxin hydrochloride | 2 |
| Riboflavin | 0.219 |
| Thiamine hydrochloride | 2.17 |
| Vitamin B12 | 0.68 |
| INORGANIC SALTS: | |
| Calcium chloride ($CaCl_2$) (anhydrous) | 116.6 |
| Copper sulfate ($CuSO_4$—$5H_2O$) | 0.0013 |
| Ferric nitrate ($Fe(NO_3)3"9H_2O$) | 0.05 |
| Ferric sulfate ($FeSO_4$—$7H_2O$) | 0.417 |
| Magnesium chloride (anhydrous) | 28.64 |
| OTHER COMPONENTS: | |
| Biotin (Sigma B4639) | 16 μM |
| Ascorbic acid (Sigma A4034) | 100 μM |
| Pantothenic acid (Sigma P5155) | 18 μM |
| Antibiotics-antimycotics (amphotericin-streptomycin-penicillin) (Sigma A7292) | 1% |
| Newborn calf serum | 10% |

6) Phenotypic Characterization

The cells are labeled in PBS buffer containing 0.2% of fetal calf serum and incubated with anti-mouse monoclonal antibodies conjugated to fluorescein isothiocyanate (FITC), phycoerythrin (PE), peridinine chlorophyl protein (PerCP) or allophycocyanin (APC), for 30 min at 4° C.

After washing, the cells are analyzed by flow cytometry (FACS or Fluorescence Analysis Cell Sorter) (FACS Calibur, Becton Dickinson, Mountain View, Calif.). The capture and the analysis of data are carried out using the Cell Quest software (Becton Dickinson).

All the antibodies (CD34, CD31, CD38, CD44, CD45, CD73, CD81, CD90, CD117, Scal and Flk1) come from BD Biosciences (Heidelberg, Germany).

For the intracellular labeling, after fixing with 4% paraformaldehyde for 10 min at 4° C., the cells are permeabilized with PBS buffer containing 1% of BSA and 0.5% of saponin (Sigma) for 20 min at ambient temperature.

Then, after labeling with anti-troponin T antibodies (Microm Microtech, clone 13-11), an anti-mouse PerCP antibody is used (BD Biosciences).

7) Immunocytochemistry

The adherent cells, cultured on slides, are washed with PBS and then fixed overnight at 4° C. in a 3.7% paraformaldehyde/PBS buffer mixture, or cooled to −20° C. in a methanol-acetone mixture (50/50).

After blocking of the nonspecific sites for 1 hour in PBS buffer containing 1% of BSA, the cells are incubated for 1 hour in a 0.3% Triton X100/PBS buffer mixture with a primary antibody: mouse antibodies directed against MLC2v (1:2, Biocytex, France), against sarcomeric α-actinin (1:500, Sigma), against anti-β-MHC (1:X), against anti-α-MHC, against titin (1:X), or against troponin T (1:100, Microm Microtech), or rabbit anti-connexin 43 antibodies (1:X, Zymed Laboratories).

After washing, a secondary antibody is added and the incubation is carried out for 60 min at ambient temperature: Alexa 546 or Alexa 350 conjugated to anti-mouse or anti-rabbit IgGs (Molecular Probes, Eugene, Oreg., dilution 1:300).

The negative controls (no staining) are carried out with purified mouse IgGs (Dako X0931) or purified rabbit IgGs (Dako X0903) and do not produce any staining.

8) RNA Extraction and Real-Time Quantitative PCR Analysis

Preferably, the quantification is carried out in real time, i.e. the detection and the quantification of the signal emitted by the probe, in particular the emission of fluorescence, are carried out during the amplification process, insofar as the increase in the signal is directly proportional to the amount of amplimers produced during the reaction.

The general principles of real-time quantitative PCR and RT-PCR, and also the various techniques for the quantitative detection of the amplimers using fluorescent probes, namely: hydrolysis of probes via the 5' nuclease activity of DNA polymerase (TaqMan™), hybridation of two probes (Hybprobes), molecular beacons and scorpion primers, are known to those skilled in the art and are in particular described in Poitras et al., Reviews in Biology and Biotechnology, 2002, 2, 1-11. Real-time quantitative PCR and RT-PCR using probes of the TaqMan™ type are in particular described, respectively, in C. Heid et al. (Genome Research, 1996, 6, 986-994) and Gibson U. et al. (Genome Research, 1996, 6, 995-1001).

Each of the probes is labeled, at at least one end, with a different fluorochrome. Preferably, the 5' end is labeled with a reporter fluorochrome and the 3' end with a quencher fluorochrome.

Advantageously, one of the ends, preferably the 3' end, of each of the probes is also labeled with an MGB (Minor Groove Binder) group, which makes it possible to artificially increase the hybridation temperature of each of the probes and thus to reduce their length.

The reporter fluorochromes that can be used for the quantitative detection are known to those skilled in the art; they are in particular: 6-FAM (6-carboxyfluorescein), TET (tetrachloro-6-carboxyfluorescein), HEX (hexachloro-6-fluorescein), fluorescein isothyocyanate (FITC), rhodamine, cyanin (CY3, CY5) and Texas red.

Similarly, the quencher fluorochromes are known to those skilled in the art: they are; in particular, methyl red and TAMRA (6-carboxytetramethylrhodamine).

More specifically, the total RNA of the cells detected as contractile in culture and the mouse heart RNA are isolated using the RNA extraction kit (RNeasy, Quiagen, France).

One μg of RNA is transcribed to DNA using the M-MLV reverse transcriptase (Invitrogen, Cergy, France) and is used in real-time PCR.

The sequences of the PCR primers are the following:

```
MEF2C
sense:
5'-AGATACCCACAACACACCACGCGCC-3'    (SEQ ID NO:1)

antisense:
5'-ATCCTTCAGAGAGTCGCATGCGCTT-3'    (SEQ ID NO:2)

Oct-3/4
sense:
5'-TCAGCTTGGGCTAGAGAAGG-3'         (SEQ ID NO:3)

antisense:
5'-TGACGGGAACAGAGGGAAAG-3'         (SEQ ID NO:4)

Brachyury
sense:
5'GACTTCGTGACGGCTGACAA-3'          (SEQ ID NO:5)

antisense:
5'-CGAGTCTGGGTGGATGTAG-3'          (SEQ ID NO:6)

Islet1
sense:
5'-CATCGAGTGTTTCCGCTGTGTAG-3'      (SEQ ID NO:7)

antisense:
5'-GTGGTCTTCTCCGGCTGCTTGTGG-3'     (SEQ ID NO:8)
```

The real-time PCR is carried out using a LightCycler rapid thermocycler (Roche, Meylan, France). The amplification carried out according to the manufacturer's recommendations.

12 µl of a reaction mixture contain 10 µl of a LightCycler-DNA Master SYBR green I mixture (FAST Start Kit comprising TaqDNA polymerase, reaction buffer, deoxynucleoside mixture and SYBR Green dye) added to 3 mM $MgCl_2$ and 0.5 µM of a mixture of appropriate primers, and 2 µl of cDNA.

The results are expressed as a function of the level of expression of the gene of interest, using a previously described mathematical model (Pfaffl et al., Nucleic Acids Res., 2002, 30, 9, e36).

The data are normalized by PCR analysis of α-tubulin (internal standard).

The amplification protocol comprises an initial denaturation at 95° C. for 8 min, followed by 40 cycles comprising a denaturation step at 95° C. for 3 s, a hybridation step at 65° C. for 10 s and an elongation step at 72° C. for 10 s.

The temperature transition rate is 20° C./s.

The fluorescence is measured at the end of each elongation step.

After amplification, a melting curve is produced by heating the product at 20° C./s to 95° C., cooling at 20° C./s to 70° C., and maintaining at 70° C. for 20 s, and then heating slowly at 0.1° C./s to 95° C.

The fluorescence is measured during the slow heating phase.

The melting curves are used to determine the specificity of the PCR products, which is conformed by gel electrophoresis.

The Student's t test is used to analyze the statistical significance. All the P values correspond to tests carried out in duplicate and $P<0.05$ values are considered to be statistically significant.

The PCR analysis can also be carried out using the DNA.

The mouse heart DNA is isolated using the QIAmp® mini extraction kit (QIAGEN).

The DNA concentrations are measured with the Nanodrop ND100 system.

The purity of the DNA is verified by absorbance measurements at 260 and 280 nm.

The real-time PCR is carried out with the AB17000 thermocycler (Applied Biosystem) to quantify the cells grafted into the mouse heart. Each reaction medium (25 µl) contains between 1 and 3 ng of genomic DNA, 0.3 µm of each primer and 2.5 µl of a 2×SYBR Green master mix (Applied Biosystem).

The data are normalized by PCR analysis of the 36B4 gene (acid ribosomal phosphoprotein PO). The nucleotide sequences of the PCR primers are the following:

```
GFP
sense:      GGGCACAAGCTGGAGTACAAC    (SEQ ID NO:9)

antisense:  TCACCTTGATGCCGTTCTTCT    (SEQ ID NO:10)

36B4
sense:      AGTCGGAGGAATCAGATGAGGAT  (SEQ ID NO:11)

antisense:  GGCTGACTTGGTTGCTTTGG     (SEQ ID NO:12)
```

The amplification protocol comprises an initial denaturation at 95° C. for 10 min, followed by 40 cycles comprising a denaturation step at 95° C. for 15 sec and an elongation step at 60° C. for 1 min. To confirm the absence of nonspecific amplification, a dissociation curve is generated from 60° C. to 95° C.

The standard curve for quantifying the GFP and 36B4 genes in the grafted mouse heart is produced by mixing the GFP DNA of the donor mouse with the C57Bl/6N DNA of the grafted mouse.

9) Model of Myocardial Infarction

Female 8- to 12-week-old C57Bl/6N mice (22 to 28 g) are used. Since they are genetically very close to the GFP donor mice [transgenic mice expressing GFP (Green Fluorescent Protein)] (Okabe M. et al., FEBS Lett., 1997, 407, 3, 313-319), an immunosuppressor treatment is not necessary.

After an intraperitoneal injection of ketamine (75 mg/kg) and of xylasine (7.5 mg/kg), the mice are subjected to a tracheal intubation so as to allow ventilation (Huga Sachs electronik ventilator, March-Hugstetten, Germany).

Gas anesthesia is maintained with isoflurane or halothane at 2%.

The surgical procedure is carried out under optical magnification (×4 and ×8).

After left thoracotomy up to the 5th intercostal space, the pericardium is opened and the left descending artery is ligatured with an 8/0 polypropylene thread (Ethicon, Johnson & Johnson, Brussels). Immediately following this, a total volume of 10 µl containing $1 \times 10^5$ cells is injected at 3 points into the ischemic region (pale region, downstream of the ligation) with a Hamilton No. 701 syringe (Reno, Nev.).

The chest is closed again and the mice are woken.

For the echocardiographic functional studies, the acute myocardial infarction model is slightly modified.

To obtain the data before (comparison point) and 3 days after the myocardial infarction, a subacute model is used.

The injections of cells or of the medium (control group) are carried out 3 days after the coronary artery has been ligatured, using the same intercostal approach. A control echograph is carried out before generation of the infarction and gives the baseline. An echograph is then carried out 3 days after the infarction and corresponds to DO. The injection of cells according to the invention or of medium is then carried out.

All the cell types tested are injected in the same amount ($10^5$) and resuspended in the same volume (10 µl).

10) Immunohistochemistry

The mice are killed by cervical dislocation under anesthesia with $CO_2$. The hearts are rapidly removed, on the 7th, 14th and 28th days, cut longitudinally along the central axis and fixed overnight at 4° C. in 3.7% or 4% paraformaldehyde. The tissue is embedded in paraffin and 6 μm sections are cut.

For the immunohistology, the tissue sections are deparaffinized for 15 minutes and rehydrated in alcohol. The endogenous peroxydase activity is inhibited by incubation in 3% hydrogen peroxide for 20 minutes, followed by 2 washes for 5 minutes in PBS. These sections are then incubated for 30 minutes in 1% BSA in PBS, and then a primary antibody: rabbit anti-GFP antibody (1:300, Molecular Probe A11122) and/or mouse anti-MLC-2v antibody (1:2) or mouse anti-troponin T antibody (1:100). As regards the latter antibody, incubation in a citrate buffer at 95° C. for 25 min is necessary before the labeling. After washing, the following secondary antibodies are used: goat anti-rabbit FITC antibody (1:500, Jackson), donkey anti-mouse Texas red antibody (1:100, Jackson), donkey anti-rabbit HRP antibody (1:500, Jackson) or donkey anti-mouse HRP antibody (1:500, Jackson). For the secondary HRP antibody, the labeling on the sections is revealed with AEC (Dako) and visualized under an inverted microscope (Leica, TMRB), and the fluorescence analysis is carried out with a confocal microscope (Zeiss, LSM 510).

11) Functional Evaluation by Echocardiography

The functional echocardiographic evaluation is carried out in the two groups, before the myocardial infarction (comparison point), immediately before the injection (DO, 3 days after the myocardial infarction), and 1 week (D7) and 4 weeks (D28) after the injection.

All the echocardiographic analyses are carried out under gas anesthesia. The echographic evaluations are carried out with the VIVID 7 echocardiographic system (General Electric) equipped with a 14 MHz linear matrix transducer (Agilent; Andover, Mass.), which makes it possible to obtain a transverse section over the left ventricle. The end-systolic and end-diastolic phases are defined as the phases in which the surface of the left ventricle is the smallest or the largest, respectively.

The left ventricular end-systolic diameter (or LVESD) and the left ventricular end-diastolic diameter (or LVEDD) are measured at the level of the papillary muscle with left ventricle M-mode tracing with a sweep speed of 200 mm/s.

Other cardiac parameters are also measured in 2-D.

The ejection fraction (or EF) is measured by the area in a single plane and calculated according to the following formula:

$$EF (\%)=[(0.85LVAD^2/LVLD)-(0.85LVAS^2/LVLS)]/(0.85LVAD^2/LVLD)\times 100,$$

in which LVAD corresponds to the left ventricular area in end-diastole; LVAS corresponds to the left ventricular area in end-systole; LVLD corresponds to the left ventricular long-axis length in end-diastole and LVLS corresponds to the left ventricular long-axis length in end-systole.

Each value is the mean of three measurements.

All the data are expressed as means±SEM.

The Student's t test is used to analyze statistical significance. All the P values correspond to paired t tests carried out for each group monitored, and to unpaired t tests for comparison of groups.

All the $P<0.05$ are considered to be statistically significant.

Example 2

Differentiation of the SVF Cells into Cells of Cardiac Type 2.1.: Standard Media The DMEM-F12 standard liquid medium containing 10% of newborn calf serum, or the BHK21 medium containing 10% of fetal calf serum, conventionally used for culturing pluripotent stem cells, were tested in comparison with methylcellulose (positive control; FIG. 1A).

Whatever the elements added (IL3, IL6, SCF, BMP2, TGF-β, possibly also with exposure to 5-azacytidine), the DMEM-F12 medium never makes it possible to obtain differentiation of the SVF cells into cardiac cells in an effective manner.

2.2. Conditions According to the Invention 2.2.1

When crude SVF cells are seeded and cultured in a BHK21 medium containing 10% of fetal calf serum and on an appropriate adhesion support or surface (gelatin), approximately 10% of the cells exhibit a cardiac phenotype estimated by spontaneous contraction of the cells and expression of troponin T (FIG. 1B). The removal of β-mercaptoethanol results in the absence of emergence of cardiac cell clusters, but the addition of this compound to other conventional culture media never induces cardiac differentiation, thereby suggesting that β-mercaptoethanol is necessary but not sufficient to engage the SVF cells in cardiac differentiation, the BHK21 medium also being important.

The frequency at which clusters of cardiac phenotype are obtained under these culture conditions is variable, but nevertheless makes it possible to obtain sufficient cardiac cells for the purpose of transplanting them.

2.2.2.

primary culture in a methylcellulose-based medium (see example 1.3) until the emergence of contractile clones (approximately 2 weeks);

selection of the contractile cells by dissection under an inverted microscope (selection both of the elongated cells and of the rounded cells);

culture of the selected clones in a BHK21 liquid medium containing at least fetal calf serum and β-mercaptoethanol, under the conditions disclosed in example 1.4), i.e. by seeding in dishes coated with gelatin and addition of the BHK21 medium.

Over the 48 hours which follow, after placing in culture in the liquid BHK21 medium, some elongated and contractile fibers are observed.

Two weeks later, approximately 60% of the cells are troponin T⁻ (FIG. 1B).

At this stage, the culture contains two distinct morphological types of cells: contractile fibers which adhere and rounded cells attached to said fibers, but mainly present in suspension and nonadherent.

The nonadherent rounded cells are not highly attached and can be recovered by collection and centrifugation of the culture medium.

The rounded cells can again be seeded in liquid BHK21; the two types of morphologies (fibers and rounded cells) will again be obtained after a few days. Careful examination of the culture derived from the rounded cells re-seeded into liquid BHK21 medium shows a high expression of troponin T (60-70%) correlated with a low expression of CD90 (3-9%).

On the other hand, the cells greatly expressing CD90 (60%) will exhibit a weak cardiac potential in culture (30% of troponin T⁺ or less). This observation is correlated with the presence of a subpopulation of small fibroblastic cells which develops in the culture medium in place of the elongated cells in the form of fibers and which are contractile.

The culture from the rounded cells in suspension was obtained after more than ten passes (n=3); however, the cells selected for characterization or grafting into the mouse are preferably obtained after 1 to 4 passes.

A long-term culture of the rounded cells (more than 15 passes, n=3) shows that these cells have a stable morphology.

The population of adherent cells can be harvested by treatment with trypsin after meticulous washing so as to remove most of the rounded cells, which remain in suspension.

To avoid the use of trypsin, it is therefore possible to obtain good expansion of the cells and to recover and re-seed the cells in suspension in the culture medium (rounded cells).

With such a procedure, $2 \times 10^8$ troponin T-positive adherent cells and $1.5 \times 10^8$ nonadherent cells can be obtained in four weeks, from one gram of fat tissue ($20 \times 10^6$ crude SVF cells) without using trypsin. This allows an extraordinary expansion. When seeded at 200 000 cells per 30-mm dish (200 000/P30), these rounded nonadherent cells become a confluent layer of $10^6$ cells with 60% of troponin T-positive cells in eight days.

Simultaneously, each plate produces 150 000 rounded cells in suspension every two days for 10-15 days, for 4-6 weeks, i.e. at least until the adherent layer ages.

2.3. Comparative Studies

Culturing of the Cells of the SVF in DMEM-F12 Medium Only:

Very few or no cardiogenic cells are obtained. The cells are lost at the first change of media (15 min to 4 h after seeding) since they adhere very little or not at all to the culture flask under these conditions. If the culture medium containing the cells that have remained in suspension is harvested, then the cardiogenic cells can be found therein, revealed by culturing in methylcellulose.

Figure 9:
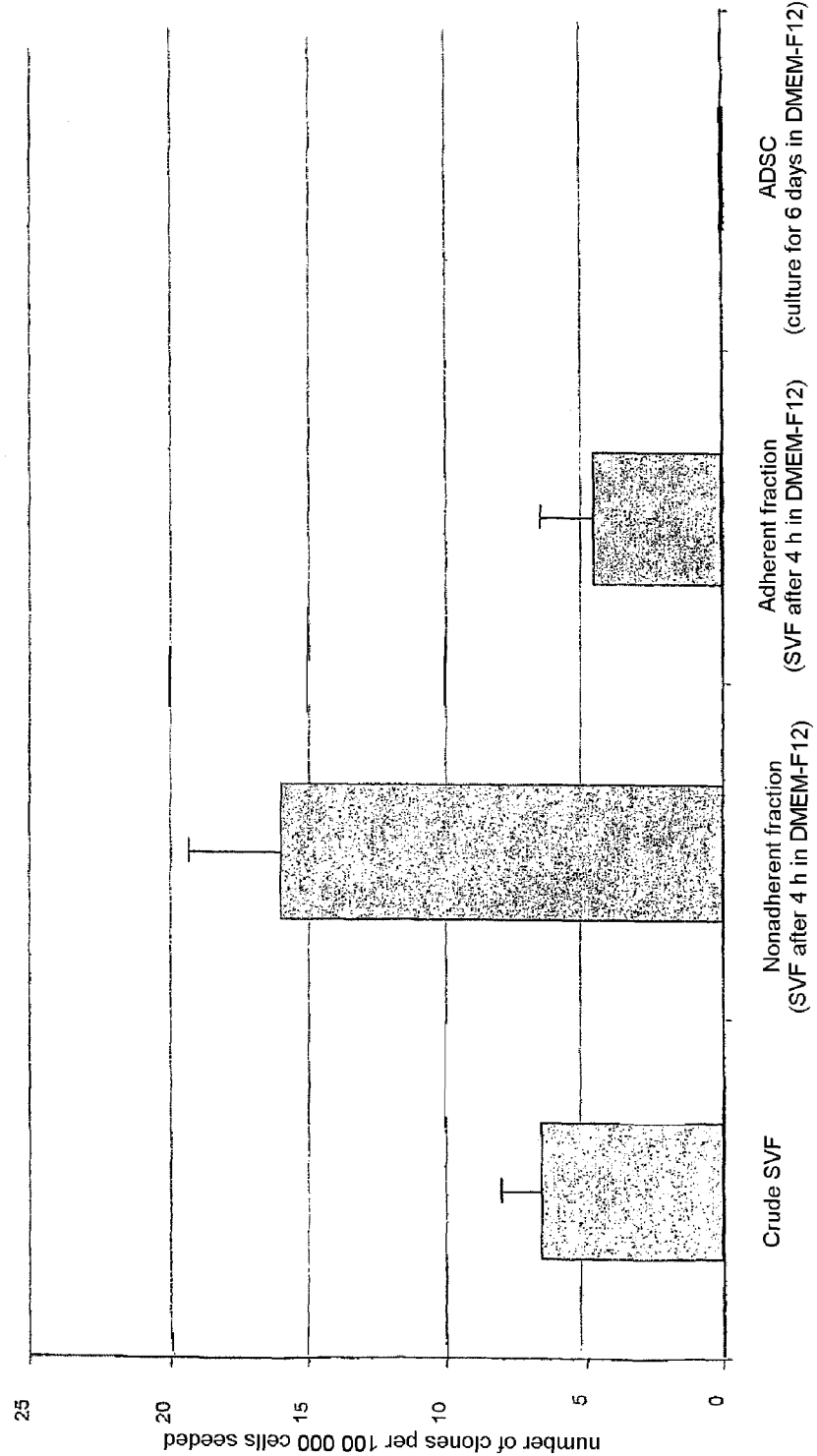
FIG. 9: Frequency of appearance of cardiomyogenic clones in methylcellulose.

FIG. 9 illustrates the frequency of appearance of the cardiogenic clones in methylcellulose.

Culturing of the Cells of the SVF in BHK21 Medium Only:

The presence of cardiogenic cells is observed.

Under these conditions, the cells adhere to the cell culture support and the culturing of cardiogenic cells is possible. However, other (non cardiogenic) cells adhere and grow in addition, and the culture is therefore heterogeneous.

Example 3

Phenotypic Characteristics of the Populations of Adherent and Nonadherent Cells: In Vitro Data The cell phenotypes are summarized in FIG. 2. It is seen that the two cell types have the following phenotypic characteristics: CD44$^+$, CD81$^-$, CD31$^-$, CD45$^-$, CD90$^-$, ckit$^-$, Flk1$^-$ and at least 50% are positive for Sca-1, troponin T and MLC-2v.

The major difference between the two cell types is that the adherent cells are positive for CD38 and CD73 (74%) and some (20%) express CD34, and are negative for MHC2, whereas this is not the case for the nonadherent cells, which are MHC1$^-$.

A high expression of troponin T is inversely correlated with a low expression of CD90 (3-9%).

Table IV below summarizes these characteristics.

TABLE IV

Phenotypic characteristics of the adherent and nonadherent cells

| | Adherent cells (elongated shape) | Cells in suspension (rounded shape) |
|---|---|---|
| CD31 | − | − |
| CD34 | +/− | − |
| CD38 | + | − |
| CD44 | + | + |
| CD45 | − | − |
| CD62 | − | |
| CD73 | + | Heterogeneous/− |
| CD81 | + | + |
| CD90 | Heterogeneous/− | Heterogeneous/− |
| C-kit | − | − |
| MLC2v | + | + (50%) |
| MHC1 | + (25-30%) | − |
| MHC2 | − | Heterogeneous |
| Sca-1 | + (50%) | + (50%) |
| Troponin T | + (50%) | + (50%) |
| Flk1 | − | − |
| Expression of: | | |
| Brachyury | + | + |
| Islet-1 | + | + |
| MEF-2c | + | + |
| Oct3/4 | + | + |

Figure 4:
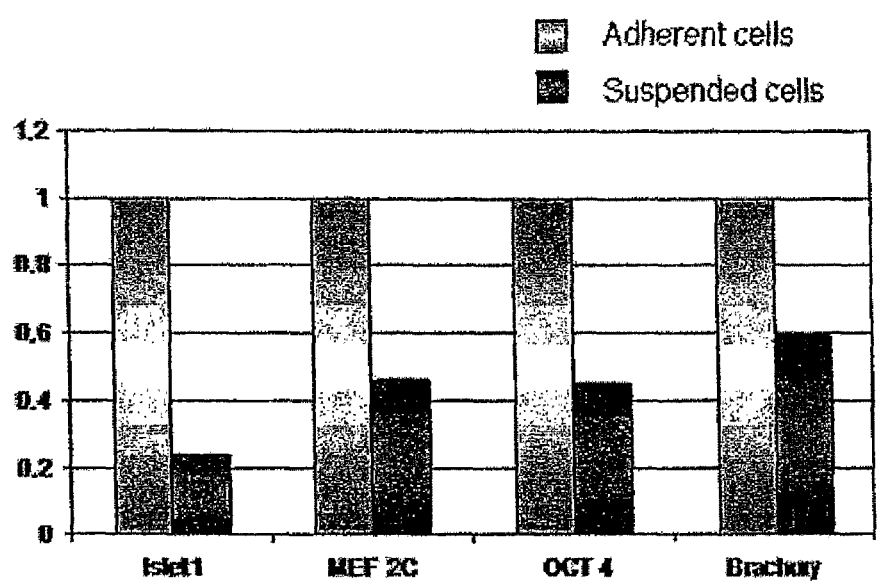
FIG. 4: Expression of genes encoding transcription factors of stem cells (Oct3/4, Islet1), of mesodermal cells (Brachyury) and of cardiac cells (Islet1, MEF2c).

The real-time quantitative PCR reveals that the two populations express the Brachyury mesodermal transcription factor, the Islet-1 and MEF-2c cardiac transcription factors and also Oct3/4, a transcriptional binding factor present in undifferentiated cells having a high proliferative potential (FIG. 4). As regards the transcripts, the level of expression is higher in the adherent cells compared with the nonadherent cells.

A concomitant identification of these markers reflects the presence of immature cells and a heterogeneity in terms of the degree of differentiation of these populations.

The protein expression as a function of cardiac differentiation is analyzed by immunohistochemistry on the adherent fibers (FIG. 4) and shows the presence of cardiac proteins such as MLC-2v, titin, β-MHC, sarcomeric α-actinin or troponin T, even though the cells do not yet express α-MHC.

These in vitro data show that the method according to the invention makes it possible to obtain large amounts of cardiomyogenic cells from adipose tissue. The cells in culture exhibit two distinct phenotypes which are nevertheless associated in culture.

Comparison of the number of cardiomyogenic cells obtained with the method according to the invention, with the number of cells obtained with the method as described in PCT International application WO 02/055678 is illustrated in Table V below. These data are obtained from 1 g of adipose tissue ($20 \times 10^6$ SVF cells).

TABLE V

| PCT International application WO 02/055678 | Invention |
|---|---|
| Culture in methylcellulose | Culture in methylcellulose + BHK21 medium |
| → 14286 clones in 1 month, i.e. $7 \times 10^6$ to $14 \times 10^6$ cardiogenic cells in 1 month. These cells can be maintained in DMEM medium (no expansion) | → $2 \times 10^8$ adherent cardiogenic cells in 1 month and $1.5 \times 10^7$ nonadherent cardiogenic cells. Possible expansion in particular by subculturing the nonadherent cells in liquid medium (many passes); in eight days, $1.5 \times 10^7$ nonadherent cells give $7.5 \times 10^7$ |

TABLE V-continued

| PCT International application WO 02/055678 | Invention |
|---|---|
| | adherent cells, themselves producing $1.1 \times 10^7$ nonadherent cells every 2 days for 4-6 weeks. |

Example 4

Use of the Adherent and Nonadherent Cells According to Example 1 for Inducing Cardiac Ischemia Repair. In Vivo Differentiation After injection of the GFP cells into a murine infarction model (conditions of example 1.8), the outcome of the rounded and elongated GFP cells is studied alone or in comparison with crude SVF-GFP cells.

The rounded cells are obtained by centrifugation of the culture supernatant. The culture enriched in adherent cells is collected after trypsinization of the adherent layer, which is washed so as to remove most of the rounded cells (see example 1).

The first group (n=6) receives $10^5$ crude SVF-GFP cells (control) and the hearts are analyzed 7 or 14 days after injection.

Whatever the time of the analysis (7 or 14 days), virtually no GFP cells are found in the mice.

Figure 5:
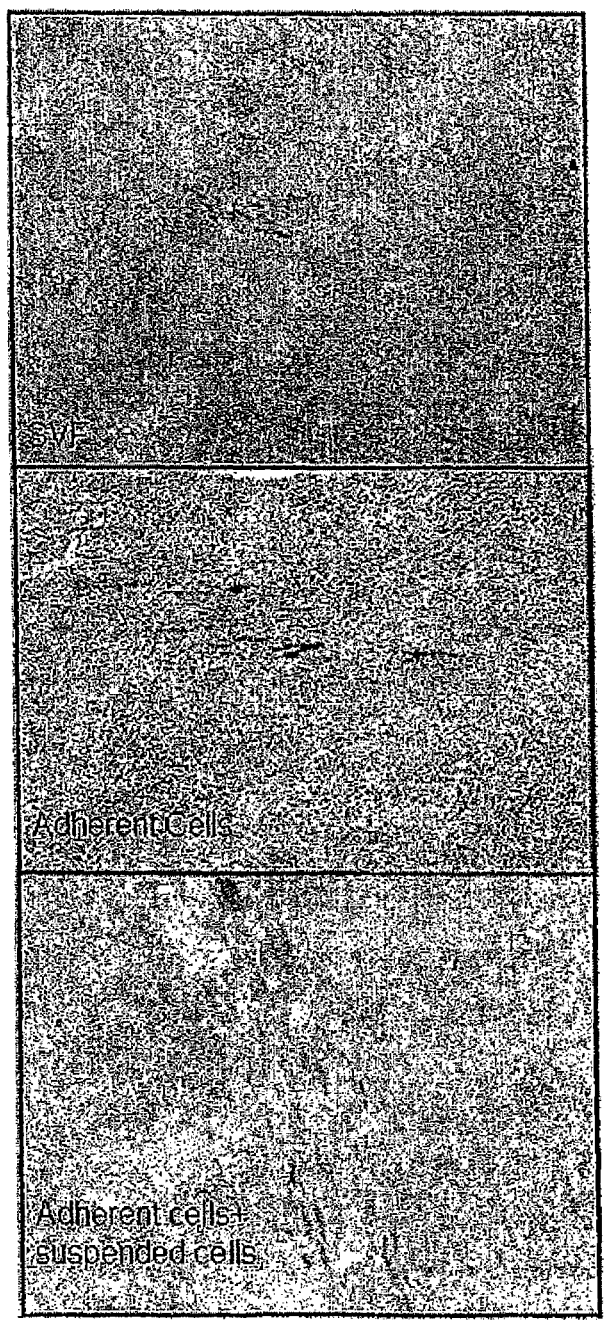
FIG. 5: Presence of cells 7 days after grafting thereof into a murin model of myocardial ischemia: immunohistochemistry revealing the presence of rare (when they are cells of the SVF cultured under conventional conditions or only the adherent cells of the cell layer) or of numerous (adherent+suspension) GFP cells in regions showing an infarction.

They always exhibit a fibroblast appearance; none of the cardiac markers are detected (FIG. 5).

The second group (n=9) receives $10^5$ nonadherent rounded cells harvested by centrifugation of the culture medium. No GFP-positive cell is detected in any of the mice of this group at 7 days (n=3) or at 14 days (n=2) after transplantation.

In the third group (n=7), $10^5$ enriched adherent cells are injected. More specifically, the cells derived from trypsinization of a cell layer obtained according to the MC-BHK21 culture method were injected. Of course, the culture was rinsed before the action of the trypsin in order to remove the maximum amount of supernatant cells. However, since the latter come from the layer, one is never sure to have removed all of them by washing, some cells which form bonds with the layer remain attached. For this reason, this population is referred to as enriched in (almost exclusively consisting of) adherent cells.

Isolated GFP cells are detected in 3 hearts out of 4 at the 7th day and in 3 hearts out of 5 at the 14th day. The morphology of these GFP cells is elongated but not of cardiac type, since no striations are observed (FIG. 5).

Figure 6:
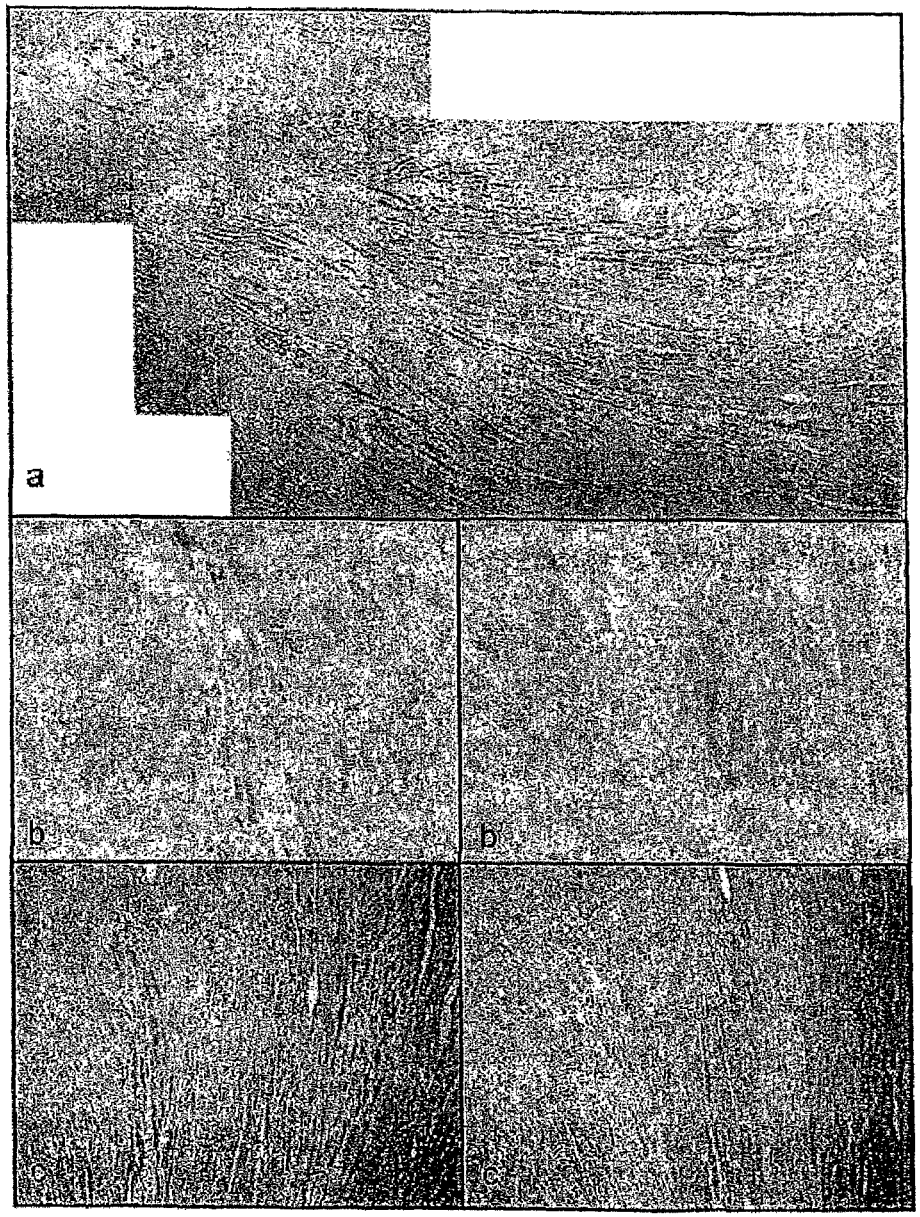
FIG. 6: Immunohistochemical identification of multiple sites where the cells are found 7 days after grafting thereof. (a) reconstitution of a region grafted with numerous GFP cells. (b, c) GFP labeling specific for cells found in the infarction along with the bordering regions, compared with the isotypic control (b', c').
Figure 7:
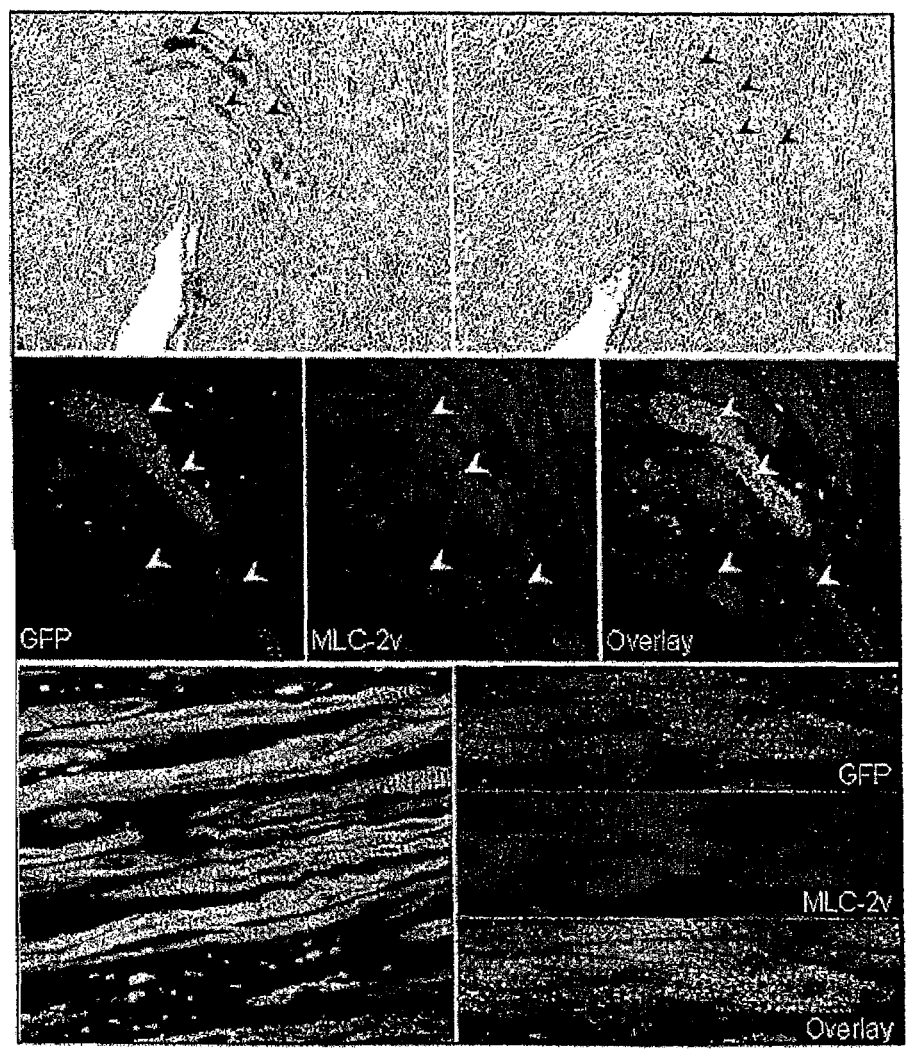
FIG. 7: In vivo cardiac differentiation: confocal immunohistochemistry showing that the GFP' grafted cells also express MLC2v, with the coexpression visualized in the overlay image, unlike the healthy tissue, which expresses only the cardiac protein (MLC2v) (see arrows). More specifically: at the top: immunohistochemistry for the presence of GFP (arrows, figure on the left) versus isotypic control (figure on the right). Middle and bottom: confocal microscopy immunofluorescence using anti-MLC2v and anti-GFP antibodies. The overlay figure shows the presence of cardiac myocytes and of cells coexpressing the GFP and MLC2v proteins (light grey).
Figure 8:
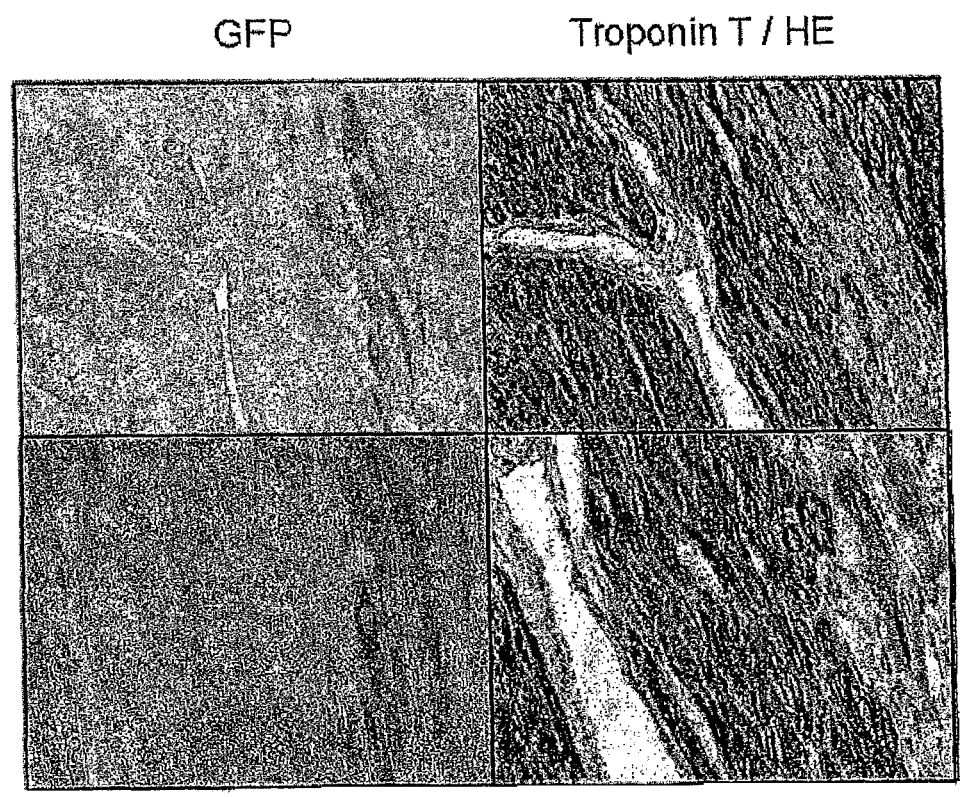
FIG. 8: In vivo cardiac differentiation: immunohistochemistry on serial sections showing that cells expressing GFP (left) and the troponin T cardiac marker (right) colocalize in the same region.

The fourth group (n=23) receives a 1:1 mixture of adherent cells and rounded cells in suspension ($1 \times 10^5$ cardiomyogenic cells express GFP, collected only between the 3rd and the 4th pass of step c); the injection is carried out immediately after the myocardial infarction by direct injection of the mixture of cells into the ventricular wall. After 7 days, the GFP cells are found in all the hearts (11 out of 11). Specific GFP labeling is observed on the edges of the region rendered ischemic, suggesting the emergence of a region of regeneration around the region rendered ischemic. Furthermore, GFP cells are also observed in the region rendered ischemic. These cells have a cardiac morphology (FIG. 6) and are in the same spatial orientation as the intact myocardium (FIG. 6). They are very abundant and form a real tissue graft of myocardium type (FIG. 6). The cells express the cardiomyocyte markers, such as MLC-2v (FIG. 7A) and troponin T (FIG. 7B).

After 15 days and one month, these cells are still present (in 5 animals out of 7) and conserve the same characteristics.

After one month, in 4 out of 5 of the hearts analyzed, the GFP-cell phenotype becomes more precise with a homogeneous morphology of striated cells.

In the group in which the mice receive both the adherent cells and the cells in suspension, the presence of GFP-positive cells expressing the cardiac cell characteristics is effectively observed in all the hearts.

This immunophenotypic characterization is reinforced by the real-time quantitative PCR analysis, based on the presence of the genomic GFP sequence.

Figure 10:
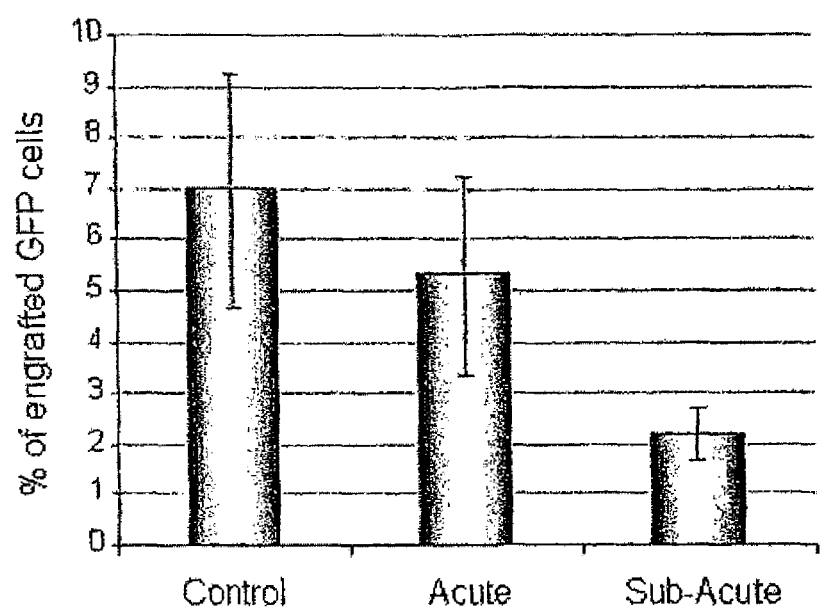
FIG. 10: Quantitative PCR to determine the grafting of GFP cells in vivo. Percentage of adherent and nonadherent cells expressing GFP, implanted into the recipient heart of the control (animal sacrificed immediately after injection) and 7 days later in an acute model of myocardial infarction.

The amount of injected GFP cells identified 7 days after administration represents 5.32%±1.955 in the acute myocardial infarction model, which corresponds to a mean of 5322 GFP cells (FIG. 10).

In comparison, in a subacute myocardial infarction model in which the cells are injected 3 days after the coronary artery has been ligatured, the percentage of grafted GFP cells at D7 is 2.2%±0.511 and represents a mean of 2201 GFP cells (FIG. 10).

A controlled experiment, in which the mice are sacrificed immediately after the cell injection, reveals that only 7% of the injected cells are found again (FIG. 10).

This amount represents 6946 cells out of the 100 000 cells injected.

In summary, the injection of 100 000 GFP cells results in the grafting of 7000 cells, and 7 days later, 5300 to 2200 GFP cells are still present, according to the myocardial infarction model involved.

In order to complete the study and in particular the influence of the ischemic environment on the graft, the mixture of the two cell populations (adherent cells and nonadherent cells) is injected into a chronic myocardial infarction (2 weeks after the ligaturing of the coronary artery).

Under these conditions, no graft is observed, as in the acute model (n=9).

The results are summarized in Table VI.

TABLE VI

Results of the grafts of cardiac cells according to the invention (adherent cells and nonadherent cells) as a mixture in a 1:1 ratio, in various infarction models

| Delay between injection and sacrifice of the animal (in days) | Acute model | Subacute model | Chronic model |
|---|---|---|---|
| D 7 | 11/11 | 2/2 | 1/5 |
| D 15 | 5/7 | 1/1 | 0/4 |
| D 30 | 4/5 | 5/9 | 0/5 |
| | cardiac cells (n = 23) | cardiac cells (n = 12) | absence of cardiac cells (n = 14) |

In order to distinguish between the effectiveness of the nonadherent cells harvested in suspension from the culture medium (n=9) versus the adherent cells obtained after trypsinization (n=7), they are injected independently, as specified above.

Surprisingly, few (using the population of nonadherent cells, FIG. 5) or no (using the population of adherent cells) GFP cells can be identified 7 or 15 days after the injection when they are administered separately.

Thus, coinjection of the two cell types is required.

The results are summarized in Table VII.

TABLE VII

Acute myocardial infarction model

| Delay between injection and sacrifice of the animal (in days) | ADSC[1] ADSC | Cardiac or cardiomyogenic cells according to the invention[2] | | |
|---|---|---|---|---|
| | | Nonadherent population | Adherent population | Mixture of the two populations in a 1:1 ratio |
| D 7 | 3/4 | 3/4 | 0/5 | 11/11 |
| D 15 | 2/2 | 3/5 | 0/2 | 5/7 |
| D 30 | — | — | — | 4/5 |
| | absence of cardiac cells (n = 6) | absence of cardiac cells (n = 9) | absence of cardiac cells (n = 7) | cardiac cells (n = 23) |

[1]ADSC (adipose-derived stromal cells): SVF cells obtained from adipose tissue and cultured for 6 days in DMEM-F12
[2]SVF cells obtained from adipose tissue, cultured in methylcellulose in order to obtain cardiac differentiation, and expanded in BHK21 medium Example 5

Functional Study

This study makes it possible to verify whether the cardiac cells according to the invention protect or restore left ventricular function in the heart rendered ischemic.

The echocardiographic evaluation made it possible to compare two groups of animals with a myocardial infarction.

Three days after surgery, one group (n=9) receives 1×10$^5$ cells (mixture of the two cell populations), while the control group receives an acellular medium (n=8).

Several parameters were analyzed in order to estimate the remodeling (based on diameters and volumes) and the systolic function (based on the left ventricular ejection fraction), in the two groups.

No significant difference is observed with regard to the left ventricular end-diastolic volume (LVEDV), the left ventricular end-systolic volume (LVESV) and the left ventricular ejection fraction (LVEF), between the two groups before and 3 days after the surgery.

Figure 11:
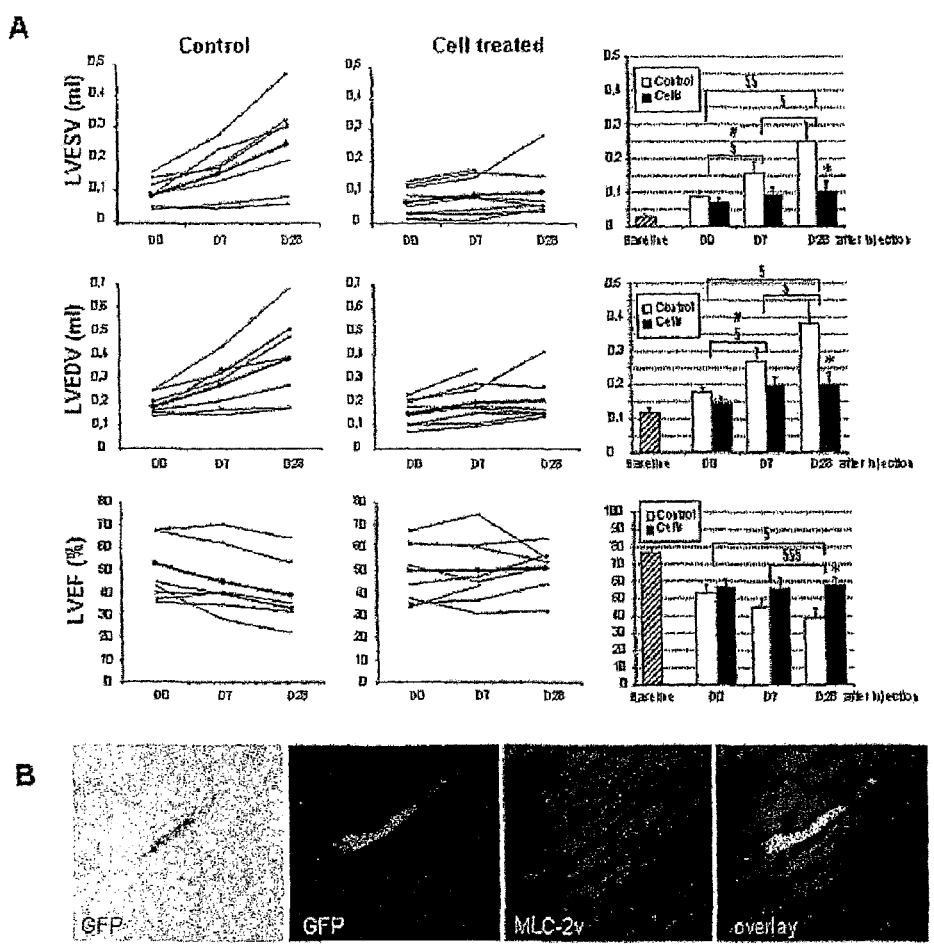
FIG. 11: Functional analysis by echocardiography. A: change in end-systolic volumes (LVESV, top), end-diastolic volumes (LVEDV, middle) and left ventricular ejection fraction (LVEF, bottom) 0, 7 and 28 days after injection of the cells or of the medium. B: comparison of the variations in functional values between D0 and D28.

Three days after ligaturing of the coronary artery and immediately before the injection (D0), the cardiac function has become deteriorated in a similar manner in the two groups (P=0.5825), indicating that the sizes of the myocardial infarctions were similar (FIG. 11).

The animals are treated either with an injection of cells or with a medium (for the control group) and the cardiac parameters are analyzed after 7 (D7) and 28 (D28) days.

In this control group, the LVEF is decreased from 52.9%±4.9 (D0) to 44.7%±5.8 at D7, and finally reaches 38.75%±5.5 at D28 (P<0.0001 D7 vs D28).

In the group treated with cells, the LVEF remains stable (56.6%±4.5 at D0; 56.4%±5.8 at D7 and 57.7%±4.4 at D28), with P=0.967, D7 vs D28.

28 days after the injection, the LVEF is significantly different in favor of the treated group, between the treated group and the control group (P=0.0201 control vs cell treatment).

As regards the remodeling, a significant dilation of the left ventricle which receives the medium is noted after 28 days, as indicated by the significant increase in the LVEDV from 0.18 ml±0.015 at D0 to 0.27 ml±0.039 at D7 and 0.38 ml±0.071 at D28 (all the P<0.03). In this control group, an increase in the LVESV is also observed: 0.0885 ml±0.015 at D0; 0.158 ml±0.032 at D7 and 0.250 ml±0.056 at D28 (all the P<0.03).

Conversely, in the myocardial infarctions treated with cells, no significant dilation is observed: 0.147 ml±0.015 at D0; 0.193 ml±0.030 at D7; 0.199 ml±0.038 at D28 for LVEDV and 0.069 ml±0.013 at D0, 0.092 ml±0.022 at D7 and 0.100 ml±0.033 at D28 for LVESV.

The comparison of the LDEDV and of the LVESV after 28 days shows a significant difference (less dilation) for the treated group vs the control group (P=0.046 and 0.039, respectively).

Better efficiency of the left ventricle at D28 is supported by the presence of cells coexpressing GFP and MLC-2v identified in 5 of the 9 hearts treated at D28 (see FIG. 11).

A higher percentage of GFP cells is quantified in the acute model compared with the subacute model of infarction, suggesting that the cells could be injected three days after the ligaturing of the artery without this having any consequence on the cell graft.

The invention claimed is:

1. A method for obtaining cardiac cells, comprising at least the following steps:
   a) selecting cardiomyogenic cells from the crude stromal vascular fraction (SVF) of adipose tissue;
   b) culturing the cells selected in step a) in a liquid medium optimized for expanding the cardiomyogenic cells ex vivo, said liquid medium being selected from the group consisting of BHK21 medium containing at least fetal calf serum and β-mercaptoethanol and any other medium, the composition of which is of the same type as that of BHK21 medium as regards the composition of inorganic salts, amino acids and vitamins;
   c) maintaining and expanding said cells by successive passes in the liquid medium; and
   d) obtaining cardiac cells.

2. The method as claimed in claim 1, wherein the selection in step a) is carried out by primary culture of cells of the crude stromal vascular fraction in a semi-solid medium, until the emergence of clusters (or clones) of contractile cells.

3. The method as claimed in claim 2, wherein step b) comprises sampling said contractile cells consisting of two subpopulations having distinct morphological types, namely adherent cells of elongated type and nonadherent cells of round (or rounded) type; and subculturing said contractile cells in said liquid medium.

4. The method as claimed in claim 3 wherein step c) comprises maintaining and expanding at least one of the two subpopulations of cells (adherent cells and nonadherent cells in suspension) by successive passes in the liquid medium.

5. The method as claimed in claim 2, wherein the semi-solid medium of step a) is selected from the group consisting of cellulosic derivatives and reconstituted basal membrane matrices comprising at least one of the following elements, collagen, laminin and proteoglycans.

6. The method as claimed in claim 2, wherein the culture time according to step a) is one to two weeks.

7. The method as claimed in claim 3, wherein, prior to the subculturing of the contractile cells, a second selection using at least one appropriate marker is carried out.

8. The method as claimed in claim 7, wherein said marker is a positive marker and/or a negative marker for cardiac cells.

9. The method as claimed in claim 8, wherein the positive marker is selected from the group consisting of MLC2v, CD44, CD81, CD73 and CD38, and the negative marker is selected from the group consisting of the major histocompatibility marker MHC2, CD31, CD45, c-kit and Flk1.

10. The method as claimed in claim 1, wherein the selection in step a) is carried out by cell sorting of the cells of the crude SVF using at least one negative marker for cardiac cells selected from the group consisting of CD31, CD45, c-kit and Flk1.

11. The method as claimed in claim 1, wherein step c) of maintaining and expanding the cells in the liquid medium is carried out according to one of the following two methods:
   centrifugation of cells in suspension in a liquid medium identical to or different than that of step b) and re-seeding of the cell pellet in the same liquid medium; or
   enzymatic detachment or any other method for detaching adherent cells, centrifugation of the detached cell suspension and re-seeding of the cell pellet in the same liquid medium.

12. The method as claimed in claim 1, wherein said cardiomyogenic cells are genetically modified.

13. A method for preparing a medicament intended for reconstituting an ischemic cardiac region which comprises incorporating into the medicament cardiac cells obtained according to the method of claim 1.

14. The method as claimed in claim 13, characterized in that said cardiac cells are selected from the group consisting of:
   (i) adherent contractile cardiomyogenic cells of elongated shape having at least one of the following characteristics: $CD38^+$, $CD44^+$, $CD73^+$, $CD81^+$, $CD31^-$, $CD45^-$, $Ckit^-$, $Flk1^-$, $MHC2^-$, approximately 50% of said cells being $Sca-1^+$, troponin $T^+$ and $MLC2v^+$,
   (ii) nonadherent cells of rounded shape having at least the following characteristics: $CD44^+$, $CD81^+$, $CD31^-$, $CD45^-$, $CD73^-$, $MHC1^-$, approximately 50% of said cells being $Sca-1^+$, troponin $T^+$ and $MLC2v^+$,
   the two types of cells also expressing the Brachyury mesodermal transcription factor, the Islet-1 and MEF-2c transcription factors and the Oct3/4 transcriptional binding factor, or
   iii) a mixture of said adherent cells and of said nonadherent cells.

15. A pharmaceutical composition comprising a mixture:
   (i) of adherent cardiomyogenic cells of elongated shape having at least the following characteristics: $CD38^+$, $CD44^+$, $CD73^+$, $CD81^+$, $CD31^-$, $CD45^-$, $Ckit^-$, $MHC2^-$, $MLC2v^+$, approximately 50% of said cells being $Sca-1^+$, and troponin $T^+$, and
   (ii) of nonadherent cells of rounded shape having at least the following characteristics: $CD44^+$, $CD81^+$, $CD31^-$, $CD45^-$, $CD73^-$, $MHC1^-$, approximately 50% of said cells being $Sca-1^+$, troponin $T^+$ and $MLC2v^+$,
   the two types of cells also expressing the Brachyury mesodermal transcription factor, the Islet-1 and MEF-2c transcription factors and the Oct3/4 transcriptional binding factor, and at least one pharmaceutically suitable carrier.

16. The composition as claimed in claim 15, also comprising one or more cardiac factors.

17. The composition as claimed in claim 16, also comprising troponin T and/or MLC2v.

18. The method as claimed in claim 1, wherein step b) of culturing the cells selected in a) is carried out in a BHK21 liquid medium containing at least fetal calf serum and β-mercaptoethanol, and any other medium, the composition of which is of the same type as that of the BHK21 medium as regards the composition of inorganic salts, amino acids and vitamins, and on an adhesion surface suitable for expanding the cardiomyogenic cells ex vivo.

19. The method as claimed in claim 1,
   wherein step a) comprises selecting cardiomyogenic cells from a primary culture of SVF cells in a semi-solid medium based on methylcellulose, and
   step b) further comprises culturing the cells selected in a) on an adhesion surface suitable for expanding the cardiomyogenic cells ex vivo.

20. The method as claimed in claim 1, wherein step a) comprises selecting the cardiomyogenic cells from the freshly prepared crude stromal vascular fraction (SVF) by primary culture of said cells of the SVF directly in BHK21 medium and on an appropriate adhesion support or surface.

21. The method as claimed in claim 18, wherein said adhesion surface is a surface coated with gelatin, adhesion proteins or extracellular matrix proteins.

22. The method as claimed in claim 8, wherein the positive marker is selected from the group consisting of CD44 and CD81, and the negative marker is selected from the group consisting of the major histocompatibility marker MHC1, CD31, CD34, CD45, c-kit, Flk1 and CD38.

23. The method as claimed in claim 1, wherein said liquid medium contains 10% fetal calf serum.

24. The method as claimed in claim 1, wherein the cardiac cells obtained by the method are a mixture of adherent cardiomyogenic cells of elongated shape and nonadherent cells of rounded shape.

25. The method as claimed in claim 24, wherein said adherent cardiomyogenic cells have at least the following characteristics: $CD38^+$, $CD44^+$, $CD73^+$, $CD81^+$, $CD31^-$, $CD45^-$, $Ckit^-$, $MHC2^-$, and $MLC2v^+$, approximately 50% of said cells being $Sca-1^+$ and troponin $T^+$.

26. The method as claimed in claim 24, wherein said nonadherent cells have at least the following characteristics: $CD44^+$, $CD81^+$, $CD31^-$, $CD45^-$, $CD73^-$, $MHC1^-$, approximately 50% of said cells being $Sca-1^+$, troponin $T^+$ and $MLC2v^+$.

27. The method as claimed in claim 1, wherein said steps a) and b) are combined and are carried out by primary culture of cells from the crude stromal vascular fraction (SVF) of adipose tissue in said liquid medium of step b), on an appropriate adhesion support or surface.

28. The method as claimed in claim 27, wherein said appropriate adhesion support or surface is a support or surface coated with gelatin, adhesion protein or extracellular matrix proteins.

29. The composition as claimed in claim 15, wherein the adherent cardiomyogenic cells and the nonadherent cells are present in a ratio of about 1:1.

* * * * *

SEQUENCE LISTING

<160> NUMBER OF SEQ ID NOS: 12

<210> SEQ ID NO 1
<211> LENGTH: 25
<212> TYPE: DNA
<213> ORGANISM: Artificial
<220> FEATURE:
<223> OTHER INFORMATION: MEF2C sense primer

<400> SEQUENCE: 1
agatacccac aacacaccac gcgcc                                           25

<210> SEQ ID NO 2

```
<211> LENGTH: 25
<212> TYPE: DNA
<213> ORGANISM: Artificial
<220> FEATURE:
<223> OTHER INFORMATION: MEF2C antisense primer

<400> SEQUENCE: 2
atccttcaga gagtcgcatg cgctt                                         25

<210> SEQ ID NO 3
<211> LENGTH: 20
<212> TYPE: DNA
<213> ORGANISM: Artificial
<220> FEATURE:
<223> OTHER INFORMATION: Oct-3/4 sense primer

<400> SEQUENCE: 3
tcagcttggg ctagagaagg                                               20

<210> SEQ ID NO 4
<211> LENGTH: 20
<212> TYPE: DNA
<213> ORGANISM: Artificial
<220> FEATURE:
<223> OTHER INFORMATION: Oct-3/4 antisense primer

<400> SEQUENCE: 4
tgacgggaac agagggaaag                                               20

<210> SEQ ID NO 5
<211> LENGTH: 20
<212> TYPE: DNA
<213> ORGANISM: Artificial
<220> FEATURE:
<223> OTHER INFORMATION: Brachury sense primer

<400> SEQUENCE: 5
gacttcgtga cggctgacaa                                               20

<210> SEQ ID NO 6
<211> LENGTH: 19
<212> TYPE: DNA
<213> ORGANISM: Artificial
<220> FEATURE:
<223> OTHER INFORMATION: Brachury antisense primer

<400> SEQUENCE: 6
cgagtctggg tggatgtag                                                19

<210> SEQ ID NO 7
<211> LENGTH: 23
<212> TYPE: DNA
<213> ORGANISM: Artificial
<220> FEATURE:
<223> OTHER INFORMATION: Islet1 sense primer

<400> SEQUENCE: 7
catcgagtgt ttccgctgtg tag                                           23

<210> SEQ ID NO 8
<211> LENGTH: 24
<212> TYPE: DNA
<213> ORGANISM: Artificial
<220> FEATURE:
<223> OTHER INFORMATION: Islet1 antisense primer

<400> SEQUENCE: 8
```

```
gtggtcttct ccggctgctt gtgg                                           24

<210> SEQ ID NO 9
<211> LENGTH: 21
<212> TYPE: DNA
<213> ORGANISM: Artificial
<220> FEATURE:
<223> OTHER INFORMATION: GFP sense primer

<400> SEQUENCE: 9
gggcacaagc tggagtacaa c                                              21

<210> SEQ ID NO 10
<211> LENGTH: 21
<212> TYPE: DNA
<213> ORGANISM: Artificial
<220> FEATURE:
<223> OTHER INFORMATION: GFP antisense primer

<400> SEQUENCE: 10
tcaccttgat gccgttcttc t                                              21

<210> SEQ ID NO 11
<211> LENGTH: 23
<212> TYPE: DNA
<213> ORGANISM: Artificial
<220> FEATURE:
<223> OTHER INFORMATION: 36B4 sense primer

<400> SEQUENCE: 11
agtcggagga atcagatgag gat                                            23

<210> SEQ ID NO 12
<211> LENGTH: 20
<212> TYPE: DNA
<213> ORGANISM: Artificial
<220> FEATURE:
<223> OTHER INFORMATION: 36B4 antisense primer

<400> SEQUENCE: 12
ggctgacttg gttgctttgg                                                20
```